(12) United States Patent
Von Oepen et al.

(10) Patent No.: US 8,524,132 B2
(45) Date of Patent: Sep. 3, 2013

(54) METHOD OF FABRICATING AN INTRALUMINAL SCAFFOLD WITH AN ENLARGED PORTION

(75) Inventors: Randolf Von Oepen, Aptos, CA (US); Kevin J. Ehrenreich, San Francisco, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 141 days.

(21) Appl. No.: 13/087,343

(22) Filed: Apr. 14, 2011

(65) Prior Publication Data

US 2012/0043703 A1 Feb. 23, 2012

Related U.S. Application Data

(60) Provisional application No. 61/324,031, filed on Apr. 14, 2010.

(51) Int. Cl.
*B29C 55/22* (2006.01)

(52) U.S. Cl.
USPC ........ 264/209.4; 264/500; 264/523; 264/320; 264/540; 264/570; 264/572; 264/573; 264/291; 264/209.3; 264/154; 623/1.15

(58) Field of Classification Search
USPC ................. 264/400, 500, 523, 535, 570, 572, 264/573, 239, 291, 138, 209.3, 209.4, 320, 264/540, 154; 623/1.15
See application file for complete search history.

(56) References Cited

U.S. PATENT DOCUMENTS

| | | |
|---|---|---|
| 5,167,614 A | 12/1992 | Tessmann et al. |
| 5,609,598 A | 3/1997 | Laufer et al. |
| 5,766,192 A * | 6/1998 | Zacca ........................... 606/159 |
| 5,851,232 A | 12/1998 | Lois |
| 5,868,783 A | 2/1999 | Tower |
| 6,231,589 B1 | 5/2001 | Wessman et al. |

(Continued)

FOREIGN PATENT DOCUMENTS

| | | |
|---|---|---|
| DE | 199 61 757 A1 | 8/2000 |
| EP | 1913901 | 4/2008 |

(Continued)

OTHER PUBLICATIONS

Rosato, D.V. (1998). Extruding Plastics—A Practical Processing Handbook. Springer-Verlag. Ch. 13 "Pipe and Tube", relevant p. 494.*

(Continued)

*Primary Examiner* — Joseph S Del Sole
*Assistant Examiner* — Lawrence D Hohenbrink, Jr.
(74) *Attorney, Agent, or Firm* — Baker Botts LLP

(57) ABSTRACT

Devices and methods for treating veins and venous conditions, such as chronic cerebrospinal venous insufficiency, are provided. In one aspect, the disclosed subject matter provides an intraluminal scaffold having a generally tubular body with a lumen defined therethrough, the tubular body having a compressed condition for delivery and an expanded condition for implant within a vessel having a distended portion, at least a length of the tubular body configured to form an enlarged portion in the expanded condition to engage a wall of the distended portion of the vessel. Methods for fabricating and using the scaffold, methods for remodeling a vein, and methods of deploying a medical device in a vessel without negatively impacting the function of a valve of the vessel, are also provided.

20 Claims, 26 Drawing Sheets

(56) References Cited

U.S. PATENT DOCUMENTS

| | | |
|---|---|---|
| 6,241,758 B1 | 6/2001 | Cox |
| 6,293,964 B1 | 9/2001 | Yadav |
| 6,299,637 B1 | 10/2001 | Shaolian et al. |
| 6,395,026 B1 | 5/2002 | Aboul-Hson et al. |
| 6,503,272 B2 | 1/2003 | Duerig et al. |
| 6,527,800 B1 | 3/2003 | McGukin et al. |
| 6,572,652 B2 | 6/2003 | Shaknovich |
| 6,808,498 B2 | 10/2004 | Laroya et al. |
| 6,811,560 B2 | 11/2004 | Jones et al. |
| 6,929,659 B2 | 8/2005 | Pinchuk |
| 7,004,962 B2 | 2/2006 | Stinson |
| 7,025,779 B2 | 4/2006 | Elliott |
| 7,041,128 B2 | 5/2006 | McGukin et al. |
| 7,090,659 B2 | 8/2006 | Aboul-Hson et al. |
| 7,179,275 B2 | 2/2007 | McGuckin, Jr. et al. |
| 7,351,256 B2 | 4/2008 | Hojeibane et al. |
| 7,357,818 B2 | 4/2008 | Deal |
| 7,387,604 B2 | 6/2008 | Case et al. |
| 7,442,206 B2 | 10/2008 | Flagle et al. |
| 7,588,596 B2 | 9/2009 | Spiridigliozzi et al. |
| 7,618,447 B2 | 11/2009 | Case et al. |
| 7,628,806 B2 | 12/2009 | Yampolsky et al. |
| 7,704,266 B2 | 4/2010 | Thinnes, Jr. et al. |
| 7,717,952 B2 | 5/2010 | Case et al. |
| 7,749,244 B2 | 7/2010 | Brucheimer et al. |
| 7,749,246 B2 | 7/2010 | McGuckin, Jr. et al. |
| 7,798,973 B2 | 9/2010 | Stahmann |
| 7,803,171 B1 | 9/2010 | Uflacker |
| 7,867,271 B2 | 1/2011 | Geiser et al. |
| 7,972,378 B2 | 7/2011 | Tabor et al. |
| 2001/0044652 A1 | 11/2001 | Moore |
| 2003/0135268 A1 | 7/2003 | Desai |
| 2003/0208227 A1 | 11/2003 | Thomas |
| 2005/0234541 A1 | 10/2005 | Hunt et al. |
| 2006/0064120 A1* | 3/2006 | Levine et al. ............... 606/153 |
| 2006/0064151 A1 | 3/2006 | Guterman et al. |
| 2006/0178694 A1 | 8/2006 | Greenhalgh et al. |
| 2006/0229695 A1 | 10/2006 | Brown et al. |
| 2006/0241739 A1 | 10/2006 | Besselink et al. |
| 2007/0112423 A1 | 5/2007 | Chu |
| 2007/0178221 A1* | 8/2007 | Sims et al. ............... 427/2.21 |
| 2007/0239251 A1 | 10/2007 | Prabhu |
| 2007/0239273 A1 | 10/2007 | Allen |
| 2007/0293939 A1 | 12/2007 | Shrivastava |
| 2008/0188887 A1 | 8/2008 | Batiste |
| 2008/0215072 A1 | 9/2008 | Kelly |
| 2008/0221664 A1 | 9/2008 | Bales et al. |
| 2008/0221669 A1 | 9/2008 | Camilli et al. |
| 2008/0234722 A1 | 9/2008 | Bonnette et al. |
| 2008/0275490 A1 | 11/2008 | Fleming |
| 2008/0300670 A1* | 12/2008 | Gueriguian et al. ......... 623/1.15 |
| 2008/0312735 A1 | 12/2008 | Thorpe et al. |
| 2009/0062840 A1 | 3/2009 | Angel |
| 2009/0069840 A1 | 3/2009 | Hallisey |
| 2009/0163987 A1 | 6/2009 | Zilla et al. |
| 2009/0210049 A1 | 8/2009 | Thielen et al. |
| 2009/0248132 A1 | 10/2009 | Bloom et al. |
| 2009/0254175 A1 | 10/2009 | Quijano et al. |
| 2009/0299403 A1 | 12/2009 | Chanduszko et al. |
| 2010/0030319 A1 | 2/2010 | Weber |
| 2010/0049239 A1 | 2/2010 | McGuckin, Jr. et al. |
| 2010/0217304 A1 | 8/2010 | Angel |
| 2010/0268260 A1 | 10/2010 | Riina et al. |
| 2012/0046729 A1 | 2/2012 | von Oepen et al. |
| 2012/0046730 A1 | 2/2012 | von Oepen et al. |
| 2012/0046731 A1 | 2/2012 | von Oepen et al. |
| 2012/0046733 A1 | 2/2012 | von Oepen et al. |
| 2012/0046739 A1 | 2/2012 | von Oepen et al. |

FOREIGN PATENT DOCUMENTS

| | | |
|---|---|---|
| WO | WO03/009773 | 2/2003 |
| WO | WO2005/058206 | 6/2005 |
| WO | WO2007/062661 | 6/2007 |
| WO | WO2007/081820 | 7/2007 |
| WO | WO2007/127802 | 11/2007 |
| WO | WO2008/066610 | 6/2008 |
| WO | WO/2008/127328 | 10/2008 |
| WO | WO2008/156468 | 12/2008 |

OTHER PUBLICATIONS

U.S. Appl. No. 13/350,529, filed Jan. 13, 2012.
U.S. Appl. No. 13/350,515, filed Jan. 13, 2012.
U.S. Appl. No. 13/087,344, Aug. 2, 2012 Non-Final Office Action.
International Search Report and Written Opinion for PCT/US2012/021329, dated Jun. 8, 2012.
International Search Report and Written Opinion for PCT/US2012/021335, dated Jul. 30, 2012.
U.S. Appl. No. 13/087,341, filed Apr. 14, 2011.
U.S. Appl. No. 13/087,342, filed Apr. 14, 2011.
U.S. Appl. No. 13/087,344, filed Apr. 14, 2011.
U.S. Appl. No. 13/087,345, filed Apr. 14, 2011.
U.S. Appl. No. 13/087,347, filed Apr. 14, 2011.
International Search Report and Written Opinon for PCT/US2011/032589 dated Jul. 11, 2011.
U.S. Appl. No. 13/087,347, Jan. 22, 2013 Non-Final Office Action.
U.S. Appl. No. 13/087,345, Feb. 27, 2013 Response to Non-Final Office Action.
U.S. Appl. No. 13/087,344, Mar. 28, 2013 Final Office Action.
U.S. Appl. No. 13/087,341, Apr. 2, 2013 Non-Final Office Action.
U.S. Appl. No. 13/087,344, Jan. 2, 2013 Response to Non-Final Office Action.
U.S. Appl. No. 13/087,345, Nov. 27, 2012 Non-Final Office Action.

* cited by examiner

METHOD OF FABRICATING AN INTRALUMINAL SCAFFOLD WITH AN ENLARGED PORTION

CROSS REFERENCES TO RELATED APPLICATIONS

The present application claims priority from U.S. Provisional Application Ser. No. 61/324,031, filed Apr. 14, 2010, which is incorporated by reference in its entirety.

BACKGROUND

1. Technical Field

This disclosed subject matter generally relates to devices and methods for treating veins and conditions related to veins. More particularly, the disclosed subject matter relates to devices and methods that are useful for treating venous anatomies to improve venous sufficiency.

2. Description of Background

Multiple Sclerosis (MS) is a debilitating disease in which the myelin surrounding the nerves is damaged, resulting in inhibition of nerve communication and impairment of physical and cognitive abilities. There is currently no cure for MS, but management of the disease has been advanced through the use of medical treatments, diet, and other non-surgical means. These treatments reflect the lack of a known cause of MS. MS sufferers apparently have a high prevalence of narrowing, twisting, or blockage of the veins that remove blood from the main extracranial cerebrospinal veins, the jugular, and the azygous venous systems. These abnormalities cause blood "refluxing", or retrograde flow, which creates reflux in the central nervous system. As a result, pooling of non-oxygenated blood can occur along with pericapillary iron deposition. Since iron is known to create free radicals that are toxic to cells, it is hypothesized that the MS inflammations may be caused by these iron deposits as seen in CVD, mentioned above. The high iron content of MS patients' brains has been confirmed. The work led to the coining of the venous disorder Chronic Cerebrospinal Venous Insufficiency (CCSVI).

Veins are thin structures that lack some of the muscular features of arteries. Thus, distension of the veins is common. In the internal jugular vein, MS sufferers can develop distension and bulging as shown in FIG. 1. These bulbs can expand, or the entire length of vessel, or a substantial portion thereof, may expand, which causes blood accumulation and reflux as described above. Further, the venous system, and particularly the jugular portion of the venous system, includes valves that operate to allow blood to flow easily in one direction but resist the backflow of blood in the opposite direction. Veins can distend near the venous valves, and this distention can occur on either side of tile valve. For example, the vein may have a barbell shape with the valve in the handle area. Thus, the valve can act as a stenosis that restricts blood now in both directions and thereby inhibits now. Poor venous drainage and the resulting deposition of iron may be a primary or secondary cause of other diseases as well. For example, beyond MS, the treatment of CCSVI can also help prevent or treat dementia, Alzheimer's disease, or other diseases of the central nervous system.

There is a need for a method that can be used to reduce the bulbs or distension within a vein in order to reduce reflux and blood accumulation and thereby treat an underlying disease. There is also a need to maintain a venous valve open since blood now through the jugular veins can be beneficial, particularly in preventing pooling of blood in the brain.

Stenting is one option for treating CCSVI because a stent placed in the anatomy would eliminate the narrowing, twisting, or blockage of the veins, and thus prevent refluxing by allowing normal drainage of blood from the brain. Traditionally, cylindrical stents have been used in the treatment of vascular disease. That is, stents in their as-cut configuration are traditionally cylindrical. The reason for this is essentially twofold. First, the cost of manufacturing a non-cylindrical stent is substantially higher using traditional processes, and second, there has not been a strong demand for non-cylindrical stents since most diseased vessels are essentially cylindrical, and any anatomical deviations can be compensated for through balloon deployment and touch-up. However, there are no stents available on the market that are sized or designed for treating the vessel conditions relevant to CCSVI and the use of cylindrical stents to do so may not be fruitful.

Stenting abnormal vessel segments with traditional cylindrical stents has at least two downfalls. First, such stents have a tendency to dislodge from the vein because the veins have low radial force and are relatively large compared to typical stent diameters. When this happens, the stent may flow downstream and cause risk to the patient if it enters the heart, another organ, or otherwise disrupts blood flow, for example. Second, a stent with a cylindrical profile may not conform fully to a bulbous vein, and there may therefore be poor scaffolding and opportunity for thrombus formation in the gaps between the vein wall and the stent. Thus, there is a need for a stent that can be deployed within non-cylindrical vessel segments that provides the advantages of good vessel conformity in unusual anatomies, and that can produce an anchoring effect within a vein to prevent stent loss.

For many of the devices that may be used for the treatment of CCSVI, access to and delivery within the jugular vein may be necessary. However, as shown in FIG. 2, even basic access to a jugular can be difficult to accomplish without damaging the venous valves. As shown, the venous valves are formed by valve leaflets which are very thin structures that tend to protrude and taper in the antegrade direction. However, since access to the patient anatomy during interventional procedures is commonly made in the radial or femoral region, a guidewire will normally be passed in the retrograde direction. Therefore, as the guidewire is passed into the vein, it may tend to catch the valve leaflets and press against them in a resistive manner. Due to the relative weakness of the leaflets, they may tear or be otherwise damages. If the leaflets tear, they may be unable to resist backflow and therefore their function will be destroyed. This same problem can occur when other devices, such as balloon catheters or other catheter devices, are passed in the same direction as the guidewire. Thus, there is a need for a method and system of accessing the jugular veins that will eliminate or minimize the risk of damaging the valve leaflets.

SUMMARY

The purpose and advantages of the disclosed subject matter will be described and apparent from the description that follows, and through the practice of the disclosed subject matter. This devices and methods disclosed herein can apply to treatment of various venous conditions, including CCSVI.

In accordance with one aspect of the present application, an intraluminal scaffold is provided. The intraluminal scaffold has a generally tubular body with a lumen defined therethrough, the tubular body having a compressed condition for delivery and an expanded condition for implant within a vessel having a distended portion. At least a length of the tubular body is configured to form an enlarged portion in the expanded condition to engage a wall of the distended portion of the vessel. As an example, the enlarged portion can have a non-cylindrical shape.

In some embodiments of the intraluminal scaffold, the enlarged portion has a barrel shape. In some embodiments, the enlarged portion of the tubular body includes a pattern of cells substantially uniform in size when the scaffold is in the expanded condition. The non-cylindrical shaped portion can be formed of a continuous curved strut. In other embodiments, the enlarged portion can have a shape selected from a buttercup shape, a bulbous shape, an hourglass shape, a dumbbell shape, a tapered shape, a flared shape, and a corrugated shape. In one particular embodiment, the enlarged portion includes a spiral-shaped wire. In certain embodiments, the enlarged portion of the tubular body in the expanded condition conforms to the wall of the distended portion of the vessel.

The intraluminal scaffold can be a conforming scaffold, a supporting scaffold, or include one or more portions that either conform or support a vessel in which it is implanted. The scaffold can be balloon expandable, self-expandable or a portion of the scaffold is balloon expandable and the other portion of the scaffold is self-expandable.

In some embodiments, the tubular body of the intraluminal scaffold further comprises a cylindrical portion in the expanded condition extending from at least one end of the enlarged portion of the tubular body. The enlarged portion in the expanded condition can have a profile larger than a diameter of the cylindrical portion in the expanded condition. The enlarged portion can be disposed at an end of the scaffold. The intraluminal scaffold can further include a second cylindrical portion extending from a second end of the enlarged portion.

In some embodiments, the enlarged portion of the intraluminal scaffold includes a bistable construction. The enlarged portion, including the bistable construction, in the expanded condition can have a profile larger than a diameter of the cylindrical portion in the expanded condition. The enlarged portion also can have sufficient flexibility to conform to the distended portion of the vessel without plastic deformation.

In some embodiments, at least a portion of the tubular member of the intraluminal scaffold is formed of a material selected from a polymeric material, a metallic material, and a shape-memory material. In certain embodiments, the cylindrical portion of the intraluminal scaffold is formed of a material different than the enlarged portion. For example, the cylindrical portion can be formed from a material that plastically deforms when expanded to the expanded condition. In certain embodiments, the scaffold is made of a degradable material, for example, a material that is capable of extravascular degradation.

In certain embodiments, the tubular body of the intraluminal scaffold includes a side opening defined therein. The tubular body can further include a side branch in communication with the side opening to accommodate a vessel bifurcation.

In one embodiment, the intraluminal scaffold includes a restraining band to induce formation of the non-cylindrical shape when expanded to the expanded condition. The restraining band can have recoil, and can be formed of a degradable material.

In some embodiments, the tubular body of the intraluminal scaffold conforms to the wall of the vessel during vessel relaxation due to adjustments in fluid flow.

In some embodiments, the tubular body of the intraluminal scaffold recoils from its initial expanded condition over a period of time greater than one day. For example, the recoil can from its initial expanded condition can result from degradation of the material of the scaffold, e.g., a degradable material.

The intraluminal scaffold can further include a therapeutic substance. The therapeutic substance can include any one or more of the therapeutic substances described in the Detailed Description below, and in particular, one or more of fondaparinux (Arixtra®), Enoxaparin, Bivaliruden, a factor Xa inhibitor, a collagenase (e.g., Xiaflex®), or endopeptidase.

The intraluminal scaffold can further include an integrated filter system.

In accordance with another aspect of the disclosed subject matter, a method of treating a condition of a vessel is provided. According to the method, an intraluminal scaffold is provided, which includes a generally tubular body with a lumen defined therethrough, the tubular body having a compressed condition for delivery and an expanded condition for implant within a vessel having a distended portion, at least a length of the tubular body configured to form an enlarged portion in the expanded condition. The intraluminal scaffold is deployed within a distended portion of a vessel with the enlarged portion of the scaffold engaging a wall of the distended portion of the vessel.

As disclosed, the scaffold is deployed in a vein, such as an internal jugular vein. The scaffold can have a length greater than the diameter of the brachiocephalic vein. The vein can have or is subject to a valve anomaly. The tubular body of the scaffold can conform to the wall of the vessel during vessel relaxation due to adjustments in fluid flow.

In some embodiments of the method, the deployed scaffold is allowed to migrate in or adhere to the wall of the vessel. Further, the tubular body of the scaffold recoils from its initial expanded condition after the scaffold migrate in or adheres to the wall of the vessel. The tubular member can be formed of a degradable material. In these embodiments, the tubular member can recoil from its initial expanded condition due to degradation of the degradable material.

In accordance with yet another aspect of the disclosed subject matter, a method of treating a condition of a vessel is provided. The method includes: providing an intraluminal scaffold comprising a generally tubular body with a lumen defined therethrough, the tubular body having a compressed condition for delivery and an expanded condition for implant within a vessel subject to a valve anomaly; deploying the scaffold within the vessel; and allowing the tubular body of the scaffold to conform to a wall of the vessel.

In some embodiments, the above method further includes allowing the scaffold to migrate in or adhere to the wall of the vessel, and can further include allowing the tubular body of the scaffold to recoil from its initial expanded condition after the scaffold migrates in or adheres to the wall of the vessel. The recoil can be resulting from degradation of the material of the scaffold if the material is degradable. Where the scaffold is made of a degradable material, the method can further include allowing the tubular body to migrate through the wall of vessel for extravascular degradation thereof.

In some embodiments of the above method, the scaffold is deployed in a vein, such as an internal jugular vein. The tubular body of the scaffold can conform to the wall of the vessel during vessel relaxation due to adjustments in fluid flow. Additionally or alternatively, the vessel can have a distended portion, and at least a length of the tubular body is configured to form an enlarged portion in the expanded condition. In these embodiments, deploying the scaffold can include engaging the enlarged portion of the scaffold with the wall of the distended portion of the vessel.

In accordance with a further aspect of the disclosed subject matter, a method of treating a condition of a vessel is provided selecting a patient demonstrating a symptom associated with a condition selected from fatigue, chronic fatigue, venous insufficiency of the leg, chronic venous insufficiency, deep vein thrombosis, Alzheimers, adult onset dementia, Parkinsons, May-Thurner, Budd-Chiari, CCSVI, and MS, and deploying an intraluminal scaffold in a vein having or subject to a valve anomaly believed to be associated with the symptom. For example, the scaffold can be deployed in a vein having one or more valves, such as veins having valves which are atypical or irregular in function or otherwise insufficient. Such valves can be associated with a neck (e.g., jugular), a leg, or a liver. As a particular example, the vein can be an internal jugular vein.

In accordance with yet another aspect of the disclosed subject matter, an intraluminal scaffold is provided. The scaffold includes a first annular element radially expandable with respect to a longitudinal axis defined therethrough, a second annular element radially expandable with respect to the longitudinal axis, and at least one axial strut connecting the first annular element and the second annular element. The at least one axial strut has sufficient flexibility to conform to a wall of a distended portion of a vessel.

In some embodiments of the above scaffold, the at least one axial strut has sufficient flexibility to conform to the distended portion of the vessel without plastic deformation. In other embodiments, at least one of the first annular element and the second annular element is plastically deformed when radially expanded. In other embodiments, the at least one axial strut is self-expandable, and at least one of the first annular element and the second annular element is balloon-expandable. In other embodiments, the at least one axial strut and at least one of the first and second annular elements are each self-expandable. In certain embodiments, the at least one axial strut is made of a material in its austenitic phase and at least one of the first annular element and second annular element is made of a material in its martensitic phase. The at least one axial strut can be made of a polymer material. In other embodiments, the at least one axial strut is made of a linear elastic material.

In some embodiments, the first annular element has a different diameter than the second annular element when in the expanded condition. In some embodiments, the first annular element or the second annular element can include a meandering pattern, such as a sinusoidal ring.

In some embodiments, the at least one axial strut defines a radially outward strength lower than that of the first annular element or the second annular element.

In some embodiments, the at least one axial strut includes a plurality of axial struts. In these embodiments, the scaffold can further include at least one radial connector disposed between and connecting a selected pair of circumferentially adjacent axial struts. The plurality of axial struts can form a bulbous shape when expanded.

In accordance with another aspect of the disclosed subject matter, a method of fabricating an intraluminal scaffold is provided. The method includes providing a tubular body with a lumen defined therethrough, at least a length of the tubular body configured to form an enlarged portion, and defining a plurality of cells in the tubular body to form an intraluminal scaffold capable of having a compressed condition for delivery and an expanded condition for implant within a vessel, the at least a length of the tubular body having the enlarged portion when in the expanded condition.

In one embodiment of the fabrication method, providing the tubular body includes extruding a generally cylindrical tube and expanding at least a portion of the cylindrical tube to form the enlarged portion. In one embodiment, expanding at least the portion of the cylindrical tube includes blow molding to form the enlarged portion. In another embodiment, expanding at least the portion of the cylindrical tube includes hydroforming the enlarged portion.

In some embodiments, the tubular body is made of a polymeric material. Alternatively, the tubular body material can include a metal or a metal alloy.

In some embodiments, providing the tubular body includes depositing tubular body material on a mandrel having a surface defining the enlarged portion. In other embodiments, defining the plurality of cells in the tubular body includes depositing the tubular body material on select locations of the surface of the mandrel. In yet other embodiments, defining the plurality of cells in the tubular body includes removing material from the tubular body, e.g., laser cutting the tubular body.

In some embodiments, the plurality of cells are uniform in size and shape. In other embodiments, the plurality of cells are nonuniform in size or shape.

In accordance with another aspect of the disclosed subject matter, a method of deploying a medical device is provided. The method includes: establishing an open condition of a valve in a vessel of a patient; moving a medical device through the opened valve; and deploying the medical device at a target site, wherein establishing the open condition, moving the medical device and deploying the medical device are completed without negatively impacting the function of the valve.

In the above method of deploying the medical device, establishing the open condition of the valve can include altering fluid flow through the vessel in the vicinity of the valve. For example, a fluid can be introduced in an antegrade direction from a location upstream of the valve to induce opening of the valve. Before introducing the fluid, the vessel can be occluded at a location upstream of the valve. Alternatively, the fluid flow can be drawn in an antegrade direction, for example, by providing suction at a location downstream of the valve, to open the valve. In either case, the medical device can be moved from a retrograde direction through the opened valve from a location downstream of the valve. In other embodiments, altering fluid flow in the vicinity of the valve includes occluding at least one body lumen proximal to and fluidly coupled with the vessel to increase antegrade flow across the valve.

Alternatively, establishing the open condition of the valve includes temporarily expanding an expandable cuff within the valve without permanently impacting the function of the valve.

In some embodiments, deploying the medical device includes using a catheter, and the method further include removing the catheter after deploying the medical device. The medical device can be an intraluminal scaffold. Further, the intraluminal scaffold can have a generally tubular body with a lumen defined therethrough, the tubular body having a compressed condition for delivery and an expanded condition for implant within the vessel, at least a length of the tubular body configured to form an enlarged portion in the expanded condition.

In some embodiments, the valve is a venous valve. The venous valve can be located in one of an internal jugular vein and an external jugular vein.

In accordance with another aspect of the disclosed subject matter, a method of deploying a medical device across a plurality of valves of a vessel of a patient is provided. A catheter is provided which has an inner shaft member and an outer shaft member co-axially disposed and axially moveable relative to each other. The catheter is positioned in a vessel having a plurality of valves including a first valve and a second valve. A distal end of the outer shaft member is advanced across the first valve without permanently impacting the function of the first valve; moving the inner shaft member axially relative to the outer shaft member; and advancing a distal end of the inner shaft member across the second valve without permanently impacting the function of the second valve.

In some embodiments of the above method, the distal end of at least one of the inner shaft member and the outer shaft member is formed with an atraumatic configuration.

In some embodiments, the method further includes delivering a medical device through the inner shaft member to a target site. The medical device can be an intraluminal scaffold. The scaffold can have a generally tubular body with a lumen defined therethrough, the tubular body having a compressed condition for delivery and an expanded condition for implant within the vessel, at least a length of the tubular body configured to form an enlarged portion in the expanded condition.

In some embodiments of the method, the plurality of valves are venous valves.

BRIEF DESCRIPTION OF THE DRAWINGS

For a further appreciation of the above and other advantages, reference is made to the following detailed description and to the drawings, in which:

FIGS. 6 through 9 illustrate methods of treating a condition of a vein according to another aspect of the disclosed subject matter, wherein FIG. 8 depicts a vein demonstrating a vein sac.

DETAILED DESCRIPTION

Figure 1:
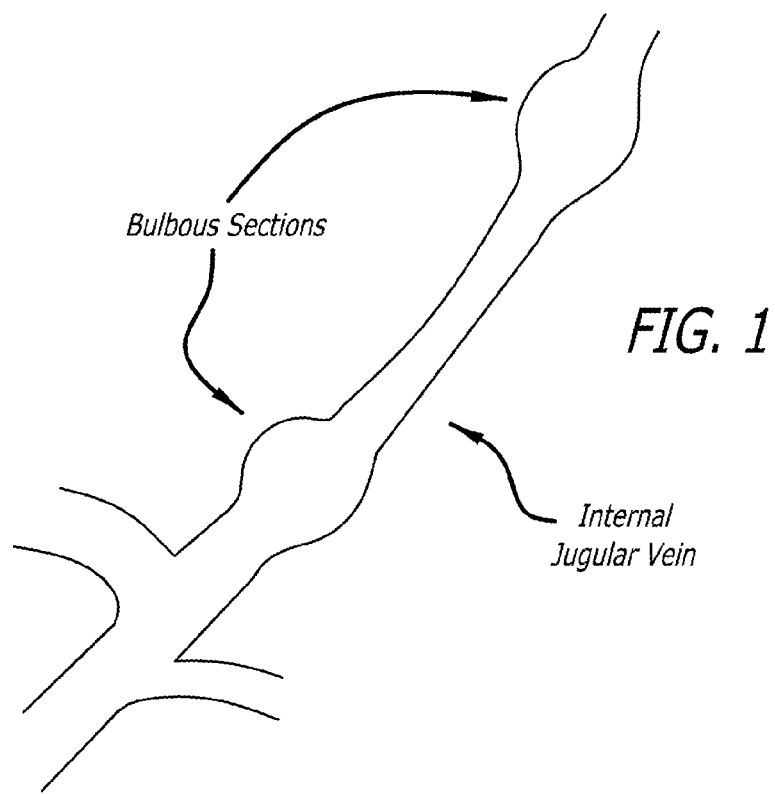
FIG. 1 schematically illustrates the anatomy of the internal jugular vein.
Figure 2:
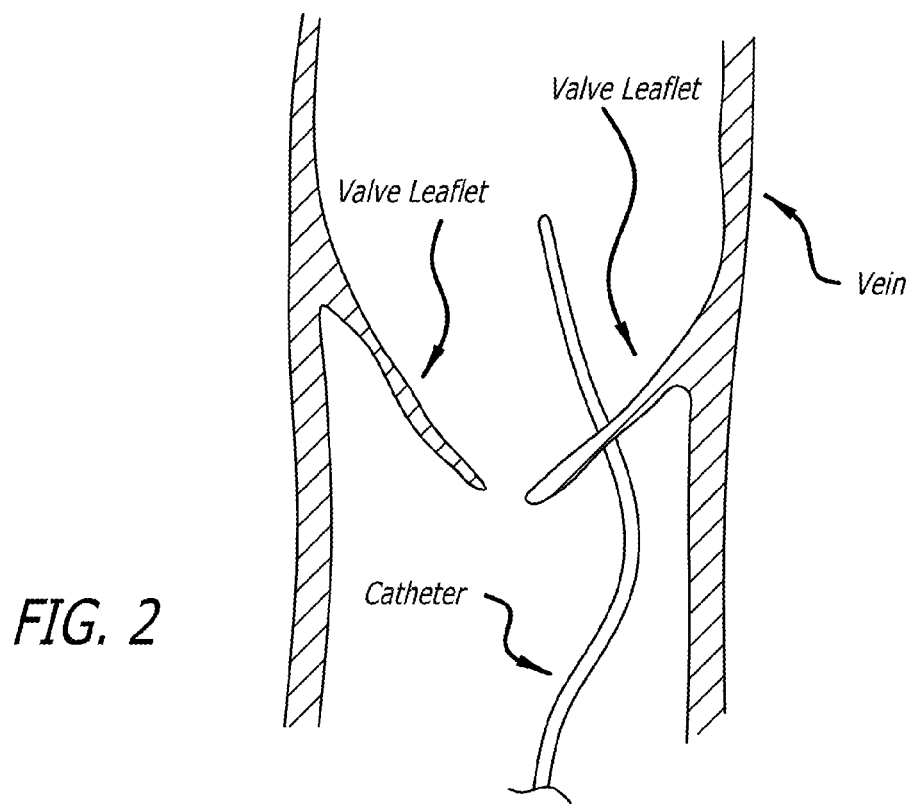
FIG. 2 schematically illustrates a scenario as a catheter is as being introduced in a retrograde direction through a valve.

While the disclosed subject matter may be embodied in many different forms, reference will now be made in detail to specific embodiments of the disclosed subject, examples of which are illustrated in the accompanying drawings. This description is an exemplification of the principles of the disclosed subject matter and is not intended to limit the subject matter to the particular embodiments illustrated.

In accordance with one aspect of the disclosed matter, an intraluminal scaffold is provided which is suitable to be implanted in a body lumen, such as a blood vessel or the like, e.g., a vein, of a patient. In general, the construction of the intraluminal scaffold can be selected such that the scaffold, or a portion thereof, can either support or conform to a body lumen. By "conforming," when the term relates to a scaffold of a portion thereof, it is intended that the overall geometry and stiffness of the scaffold, or relevant portion thereof, are such that the scaffold (or the portion thereof) can engage the lumen wall to inhibit movement of the scaffold within the lumen under the normal use conditions without substantially altering the diameter of the lumen from its undisturbed or natural state prior to implanting the scaffold. However, the conforming scaffold can be suitably sized and flexible to maintain engagement with the vessel wall in response to a change in the diameter of the vessel between its smallest diameter to its maximum anticipated diameter corresponding to different physiological states of the patient. The conforming scaffold does not urge or otherwise support the lumen wall in a predetermined diameter, but rather dynamically changes its shape to adapt to the varying size of the lumen (e.g., a blood vessel) at different anatomical sites and in different physiological conditions, and this allows for easy deployment, retrieval, and repositioning of the conforming scaffold within the blood vessel. In contrast, a supporting scaffold is usually configured for maintaining the patency of a vessel, such as an artery, and is greater in radial strength and stiffness. The scaffolds disclosed herein can be either a supporting scaffold or conforming scaffold, or include portions that have the characteristics of either a supporting scaffold or a conforming scaffold. Thus, the term "scaffold" encompasses "stent," and the two terms are used interchangeably herein. The scaffolds or stents described herein can include structural patterns used for conventional stents such as those formed by a series of longitudinally arranged rings formed by interconnected struts and connected with longitudinal connectors. However, the structural elements of the scaffolds or stents of the disclosed matter are not restricted to the struts or connectors or traditional stents, but likewise include flexible or pliant filaments, wire, and the like.

Accordingly, one aspect of the disclosed subject matter provides an intraluminal scaffold is provided. The intraluminal scaffold has a generally tubular body with a lumen defined therethrough, the tubular body having a compressed condition for delivery and an expanded condition for implant within a vessel having a distended portion. At least a length of the tubular body configured to form an enlarged portion in the expanded condition to engage a wall of the distended portion of the vessel. In another aspect, the disclosed subject matter provides a method of treating a condition of a vessel, such as a vein, which includes deploying such a scaffold within a distended portion of a vessel such that upon the deployment the enlarged portion engages a wall of the distended portion of the vessel. The enlarged portion can have a non-cylindrical shape. The vessel can be a vein, e.g., an internal jugular vein, wherein the vessel can have or is subject to a valve anomaly (e.g., one or more valves in the vein are malformed or malfunctional). This method will be described in conjunction with the intraluminal scaffold below, and it is understood the method is generally applicable for any of the various embodiments of the intraluminal scaffold described herein.

Figure 3:
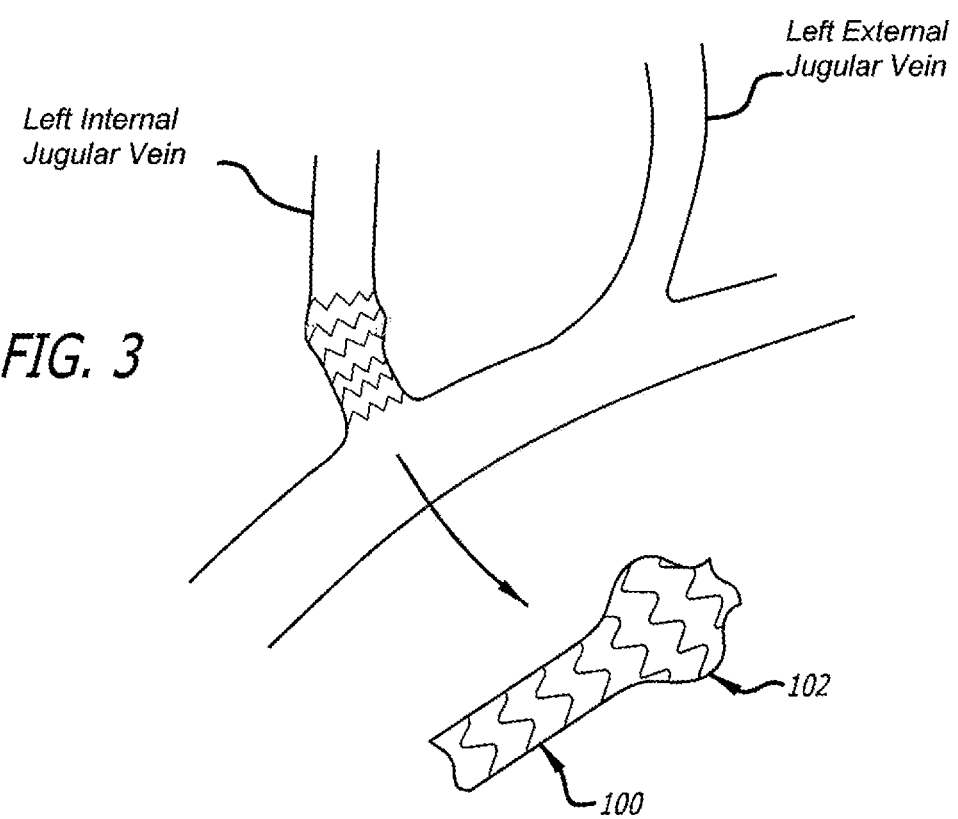
FIGS. 3-5 illustrate intraluminal scaffolds and methods of use thereof for treating a condition of a vein according to one aspect of the disclosed subject matter.
Figure 4:
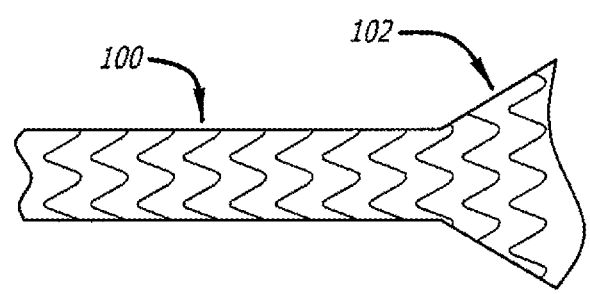

For illustration and not limitation, various embodiments of the intraluminal scaffold and related delivery systems of the disclosed subject matter are described below in connection with the drawings. It is noted that the figures are not to scale and certain dimensions have been exaggerated for clarity. Referring to FIG. 3, a stent 100 has a distal end enlarged portion 102 with an increased profile in an expanded condition (a bulbous portion is depicted for illustration purpose). This enlarged non-cylindrical portion can prevent the stent 100 from dislodging from the vein that it is deployed within. For example, the stent can be positioned within one of the internal jugular veins, wherein bulbous segment of the stent 100 will act to retain the stent within the veins. Veins are typically more elastic than arteries and thus may require additional anchoring to keep the stent 100 in place. The closely conforming feature of the stent in accordance with the disclosed subject matter may reduce thrombus formation within the vein, which may otherwise occur if a gap left between the stent and the vessel wall. The non-cylindrical portion as described herein can be embodied in many different geometrical configurations, for example the non-cylindrical portion may be embodied as a flared portion as shown in FIG. 4. Other geometrical configurations contemplated herein may have a conical or tapered appearance, or take other shapes as further described below.

Figure 5:
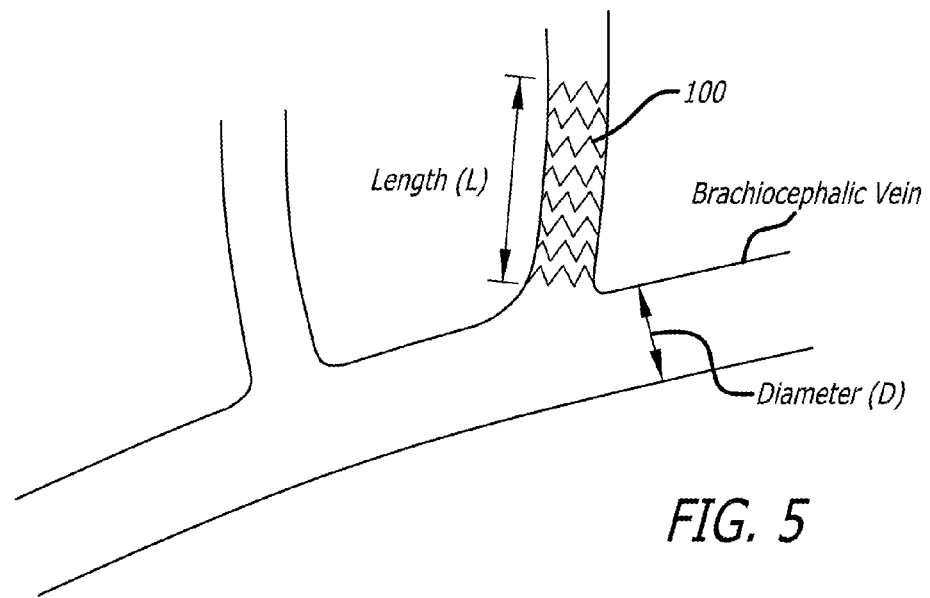

As previously described, veins are more elastic than arteries. Even with the use of the anchoring techniques, it is possible that the stent could still dislodge when used in the venous system. Accordingly, stent 100 can be sized and configured to have an expansion profile that approximates the average diameter of the target vein and a total length that is sufficient to prevent the stent from being dislodged into the brachiocephalic veins, in the event of stent dislodgment. The stent length (L) can be at least as long as the diameter (D) of the brachiocephalic vein at the ostium of the target vein. Alternatively, the stent length can be 2-4 times that diameter. This feature is illustrated further in FIG. 5. For example and not limitation, stent 100 can have radial strength tuned to the properties of the target vein. Since the elasticity of the vein is greater, the stent 100 can be a conforming stent rather than a supporting stent.

Access to the target veins that include the most anatomical abnormalities can be accomplished in a number of manners. In order to access the right internal jugular with a larger profile stent, a catheter can be delivered through and tracked the inferior vena cava. Once near the jugular, the catheter can be advanced directly into the right internal jugular vein from the superior vena cava, or it can be advanced into the left internal jugular via the brachiocephalic vein. Alternatively, when using a small profile stent delivery system, e.g. with a balloon expandable stent, access can be made through the subclavian vein in the wrist. A delivery catheter can then be tracked to the right internal jugular vein, or it can be advanced into the left internal jugular vein via the brachiocephalic vein.

The stent 100 can be formed from various materials. For example, the stent 100 can be formed of a balloon expandable material such as stainless steel, silver, platinum, tantalum, palladium, cobalt-chromium alloys such as L605, MP35N, or MP20N, niobium, iridium, any equivalents thereof, alloys thereof, and combinations thereof. Alternatively, it can be a self-expandable stent material such as nickel-titanium, copper-zinc-aluminum, or copper-aluminum-nickel. In addition, the material can be a shape memory material, a polymeric material, a degradable material, e.g., a biodegradable material, a resorbable material, and the like. Further, different portions of the stent can be formed of different material.

The material can be selected according to target anatomy. If the target anatomy has a large diameter, it may be preferable to use a self-expanding stent that can accommodate large vessels. However, smaller veins may benefit more from balloon expandable stents. Also, considerations such as the target vessel elasticity can be taken into account. In cases where the vessel is more elastic, it may be preferable to use a self expanding stent, and vice versa.

In an alternative embodiment, the stent may have an integrated filter system. For example, a parachute basket can be attached to one or more stent rings such that deployment of the stent within a vein will cause the basket to canopy across the vein. Therefore, any thrombotic material that is dislodged during placement would travel into the basket and be captured, thereby preventing a thrombotic event. Alternatively, an embolic protection device may be used during stent deployment to capture any acute thrombus and remove it from the body following stent placement.

Figure 27:
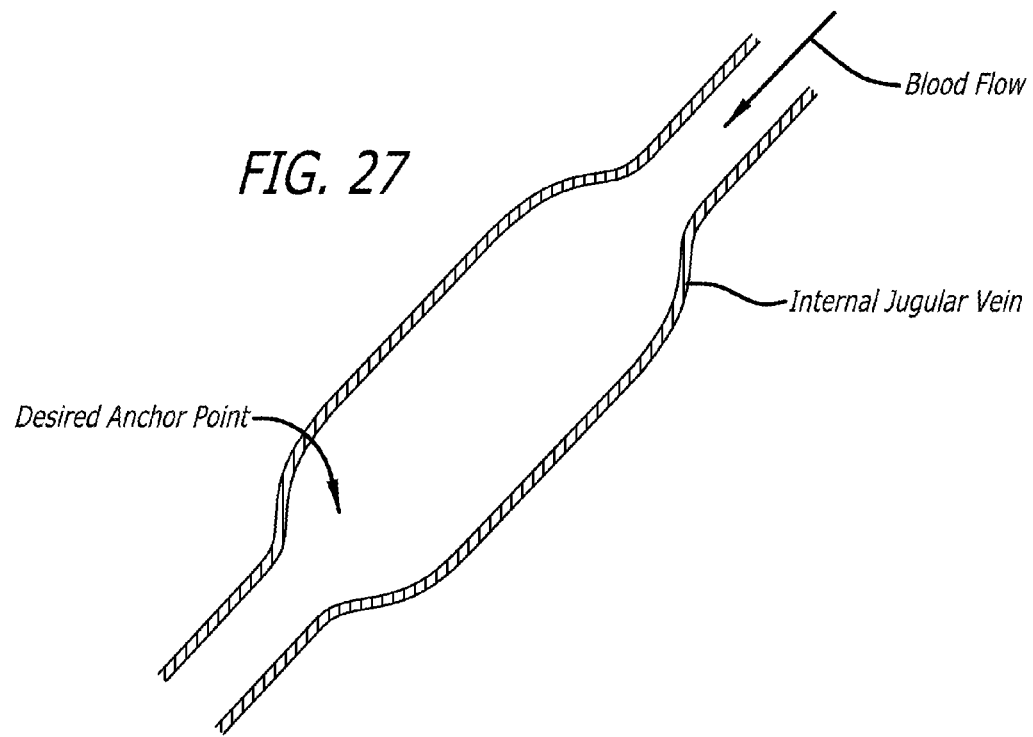
FIGS. 27 through 37 illustrate various embodiments of an intraluminal scaffold including an enlarged portion according to the disclosed subject matter.

As described above, the enlarged portion of the stent can be use as an anchor to retain the stent within a body lumen, e.g., a vein. As illustrated in FIG. 27, the desired anchor point when treating CCSVI can be near the bulbous segment in the proximal area of the internal jugular vein. It will be appreciated that this location is selected for illustrative purpose only, and the stent can be positioned elsewhere.

Figure 28:
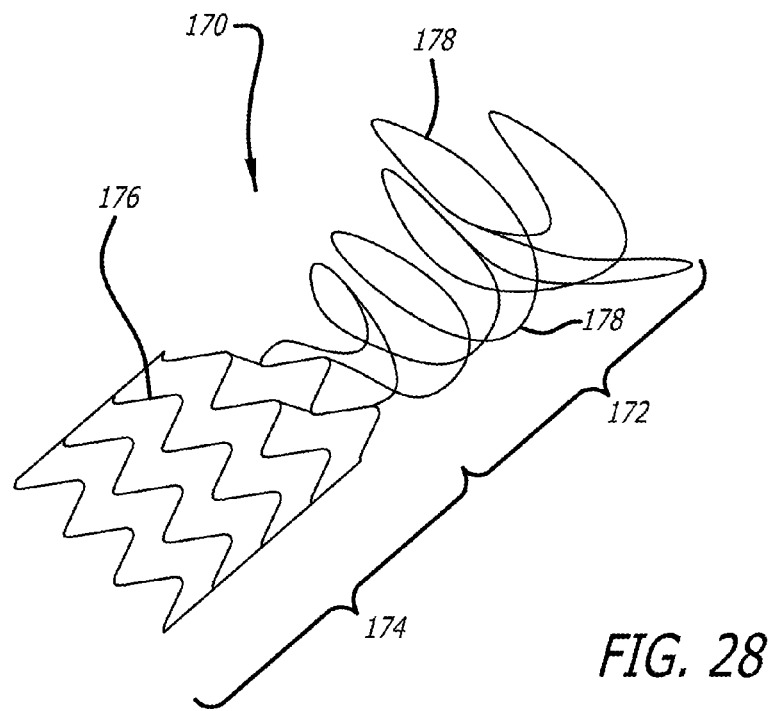

As illustrated in FIG. 28, the enlarged portion can include a spiral-shaped element 172 used as an anchor to stabilize a stent 170 within a vein. An advantage of a spiral anchor is its ability to conform to a wide range of vessels without exerting excessive radial load to the vessel wall. The stent embodiment may include one portion 174 that comprises one or more typical stent rings 176. That is, the portion 174 can include a generally meandering stent ring pattern connected with adjacent stent rings. This portion 174 of the stent 170 can be positioned within the distal segment of the vein beyond the desired anchor point. The stent 170 will then be anchored in place by the spiral anchor 172 segment that is intended to be positioned within the bulbous segment of the vein. The spiral anchor 172 can be formed by one or more spiral elements 178 that extend in a proximal direction from the normal stent segment 174. The spiral segment(s) 178 may gradually increase in diameter, thereby ensuring that they will remain in contact with the distended vessel and anchor the stent 170 within the vessel.

In an alternative embodiment, multiple spiral anchor segments 172 can be used to provide greater apposition with the vessel and therefore better anchoring. The multiple spiral anchors 172 can be connected with one another, for example by attaching the spirals at their ends. Alternatively, they can be completely independent from one another. The spirals can be formed from the same tubing as the normal stent segment, or they can be formed separately and then added to the stent segment 174 through the use of welding or other bonding processes.

Figure 36:
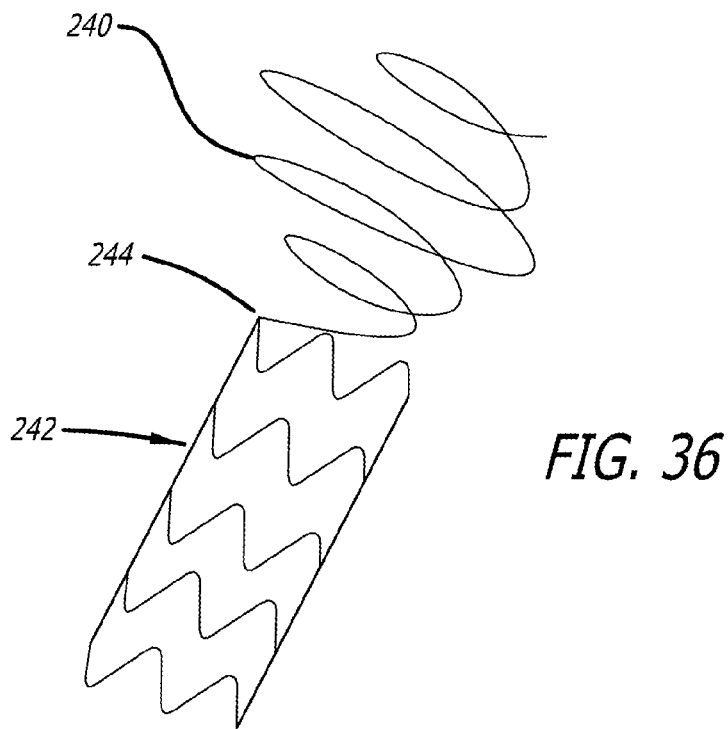

As shown in FIG. 36, a spiral anchor 240 having a bulbous profile can be used to anchor the stent 242 more particularly within a bulbous vein segment. One or more spiral anchors 240 can extend from the end 244 of the stent 242 and be formed in a spiral or curvilinear manner that first expands in diameter and then reduces in diameter. Thus, the spiral anchor 240 will conform to a bulbous segment of a vein.

Figure 29A:
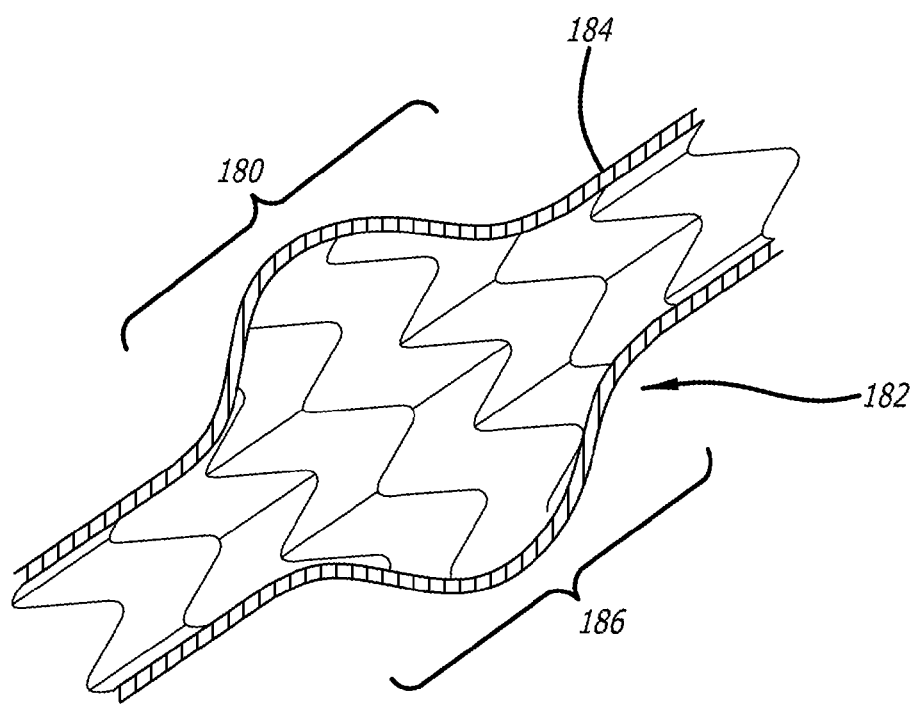

Referring to FIG. 29A, the enlarged portion of the stent can be a bulbous anchor 180 to secure the stent 182 within a vein. The bulbous anchor can have a generally barrel shaped profile as depicted. The barrel shape can be the result of a shape memory effect introduced during stent manufacturing, or it can be the result of expansion by a barrel-shaped balloon. In either case, the stent design can provide that upon expansion, the individual cell area is approximately equivalent or uniform throughout the stent structure. In other words, even though individual rings across the stent structure have varying diameters, the intracellular area remains unaffected and therefore the vascular scaffolding is more consistent than would be the case if a typical stent design were deployed into a barrel shape. Further more, use of a barrel-shaped stent with more uniform cellular structure will provide more consistent radial strength over the stent length.

Figure 29B:
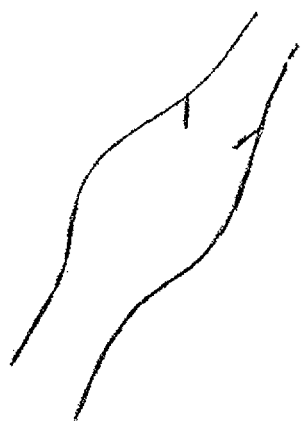

As shown in FIG. 29B, the stent can be particularly useful in the treatment of veins that are bulged or distended. This distension can occur, for example, near a venous valve. This is particularly true when the patient presents with venous insufficiency. It is notable that the bulging of the veins can be immediately adjacent to the valve, or the valve can be within the bulbous region. Often, the valve is stenosed and closed under these circumstances. Thus, in a method of using the stent (or any of the other stents described herein), the stent can be placed across the valve, wherein the stent may be placed across the valve where the stent is placed in only the distended region, or, in both the distended region and the valve segment.

Figure 29C:
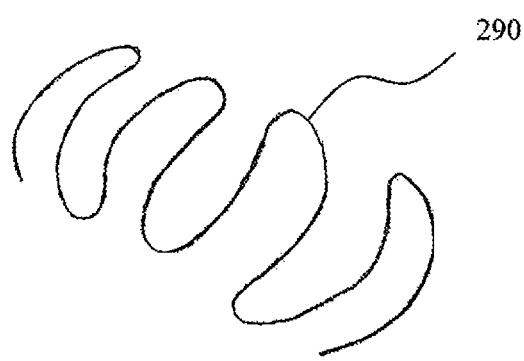

Referring to FIG. 29C, in an alternative embodiment the stent can include only one, or very few, stent rings 290. In addition, the stent ring itself can be formed with a barrel shape. Therefore, each individual strut can be curved in a way that creates annulus having a barrel shape. The length of the struts can be varied depending on the design to produce a stent that is longer or shorter, for example. Deployment of a stent structure such as the one illustrated in FIG. 29C within a vessel can conform to or support a distended region with lower risk of dislodgment.

Figure 30:
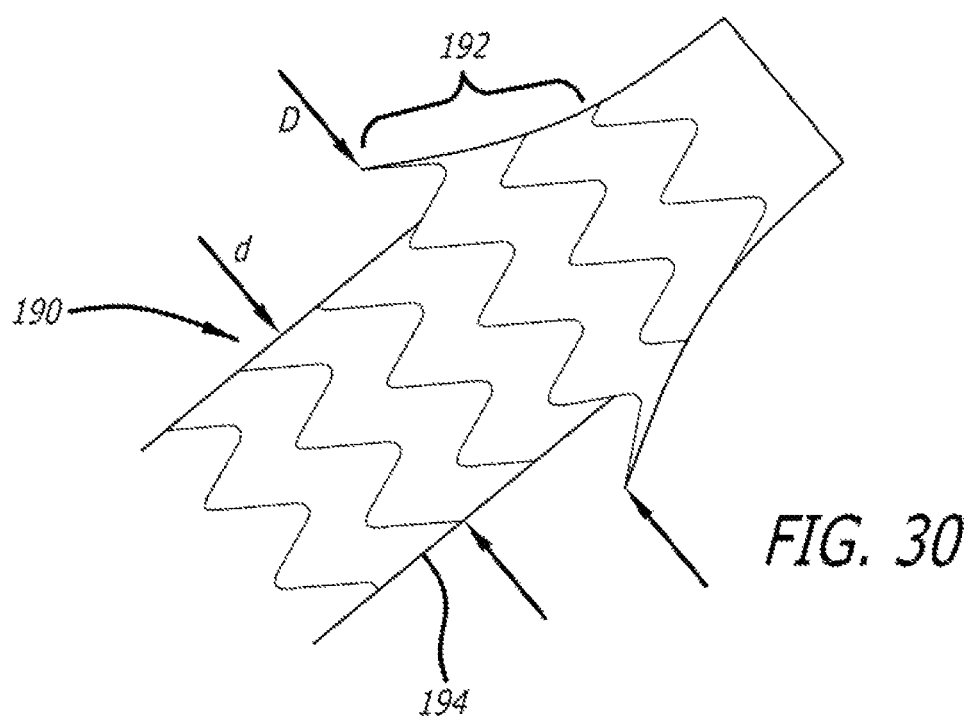

As shown in FIG. 30, the enlarged portion can include buttercup anchor for securing the stent 190 within a vein. The buttercup design contemplates that a segment 192 of the stent will be tapered outward. This flared portion 192 will have a larger profile or diameter (D) as compared to the diameter (d) of the normal stent segment 194. This structure creates an anchor that resists movement in at least two ways. First, the larger diameter D formed by the outwardly extending struts of the stent 190 is intended to provide some frictional load against the vein wall that resists dislodgment. Second, since the flared portion projects in a certain direction, it will preferentially resist motion because the flares will engage the tissue wall and expand even further if moved in the direction of the flare expansion.

Figure 31:
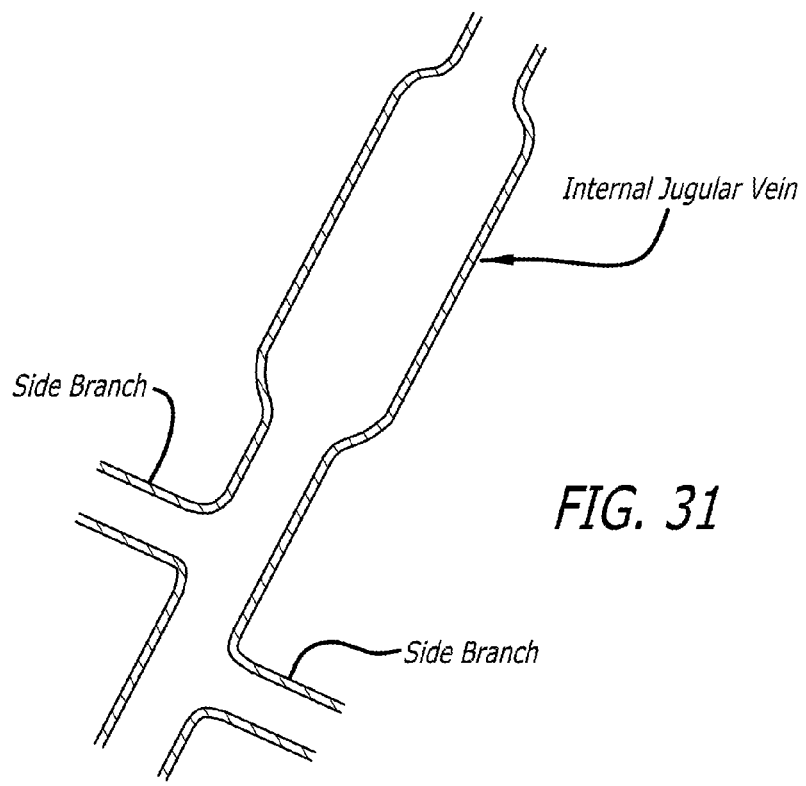
Figure 32:
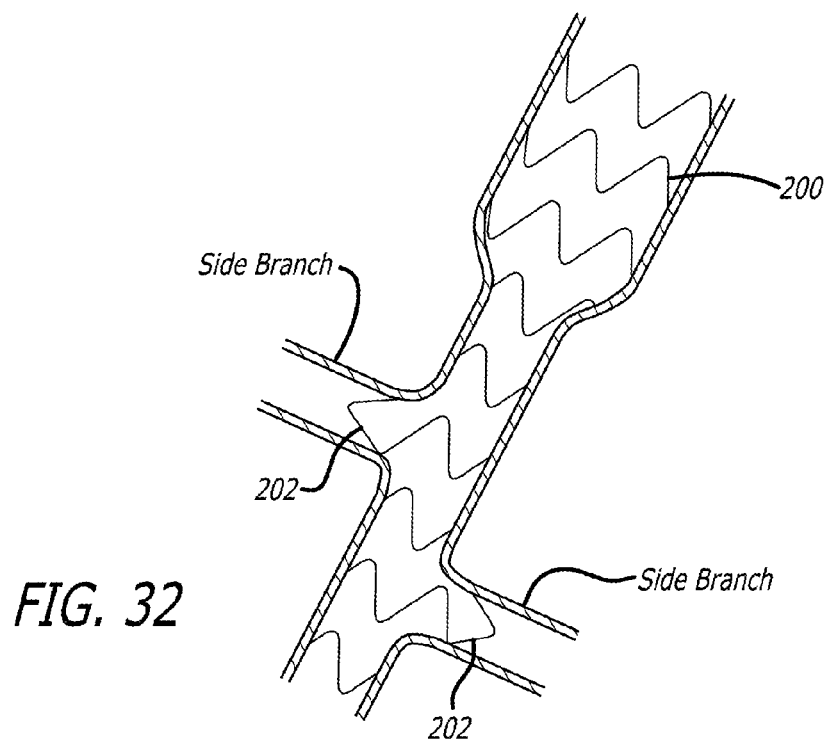

FIGS. 31 and 32 illustrate a stent where the non-cylindrical shaped portion can include a branched portion. The branched portion can be formed by one or more annular rings of the stent protruding outward from the branch location forming a surface irregularity, or by a side branch in communication with a side opening of the stent. The branched portion can engage a vessel bifurcation in order to prevent stent dislodgment. FIG. 31 indicates an exemplary anatomy in the region of the internal jugular vein. There can be one or more collaterals or side branch veins that parallel the internal jugular vein. As shown in FIG. 32, these branches allow a stent 200 to be used with side branch segments 202 that can engage the collaterals. Once these collaterals are engaged, it is more difficult for the stent to dislodge because the dislodgment force exerted on the stent by the blood flow is resisted by the reaction force that the side branch vessels apply to the stent. Thus, the stent 202 is substantially more secure within the vein.

Figure 33:
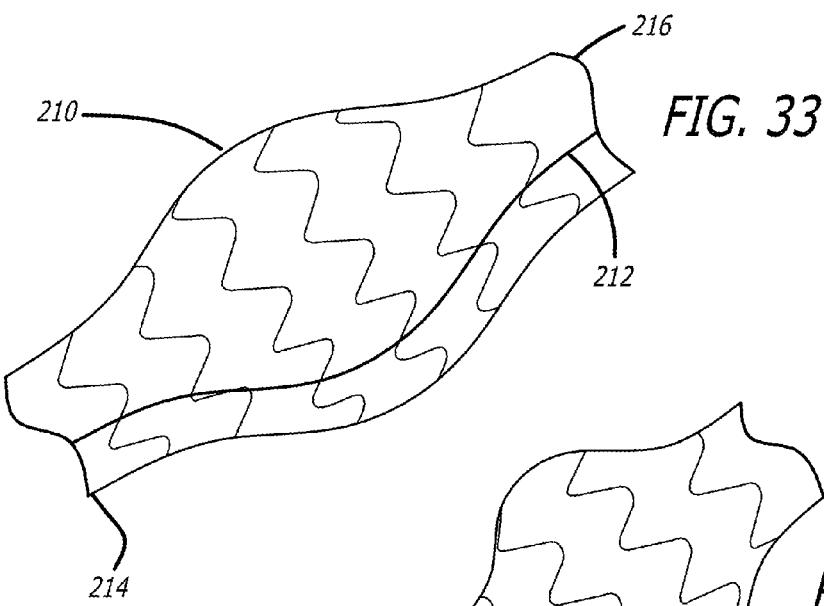

FIG. 33 shows a stent 210 showing a braided stent design that utilizes a restraining band 212 to produce a compressive load on the stent structure following deployment. This compressive load induces the formation of a bulging of the stent that creates an anchor point in the vessel. The restraining band 212 can be fabricated from an elastomeric material and bonded to the ends 214 and 216 of the stent 210 using a thermal or chemical bond. Alternatively, the band 212 can be mechanically restrained by inserting it and heat staking it within a groove or hole (not shown on FIG. 33) within the stent 210. In order to prevent the stent 210 from expanding prior to deployment, the stent can be delivered from a constraining tube, such as those used for self-expandable stents. Once deployed from the tube, the band 212 can be released and allowed to recoil and compress the stent to form the desired non-cylindrical shape. The band can also be made of a degradable or resorbable material, which can weaken over time to allow the stent to recoil to a smaller profile.

Figure 34:
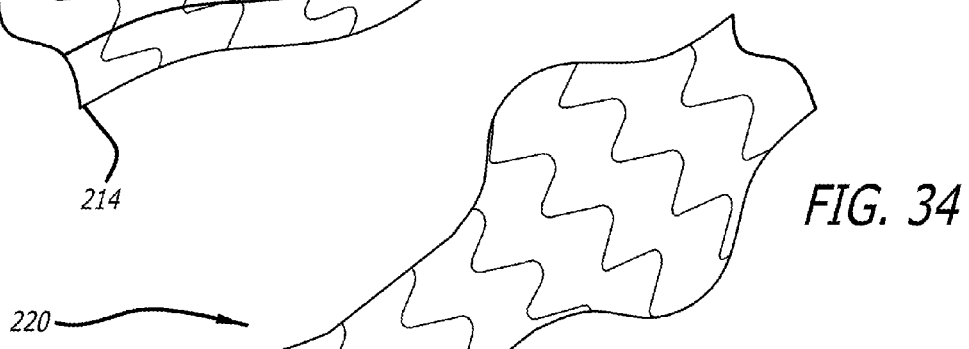

As shown in FIG. 34, a dumbbell shaped stent 220 can be used to anchor within a vein. In this embodiment, the stent can be cut from tubing with a non-cylindrical form, or alternatively, the stent can be formed from a cylindrical tube that is subsequently formed into a dumbbell shape through heat treating or mechanical strain processes. These methods of manufacturing a stent bulge will be further discussed below.

Figure 35:
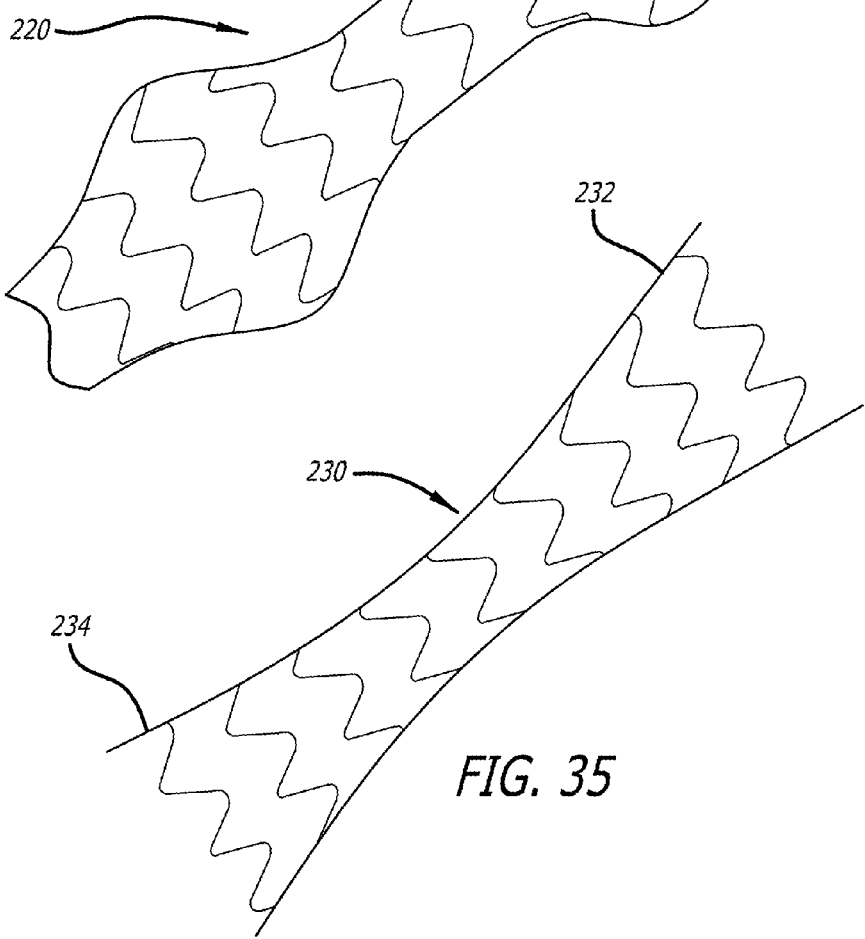

Referring to FIG. 35, stabilization of the stent can be facilitated through the use of an hourglass anchor design. Like the dumbbell design above, an hourglass shaped stent 230 may also be formed from non-cylindrical tubing. However, only the ends 232 and 234 of the stent need be tapered, thus it can be easier to form the tapers after stent cutting than it is to form bulbous segments. This is because the tapers can be formed simply by advancing the stent over a taper and introducing sufficient heat or stress to cause the portion to heat set to the new shape.

Figure 37:
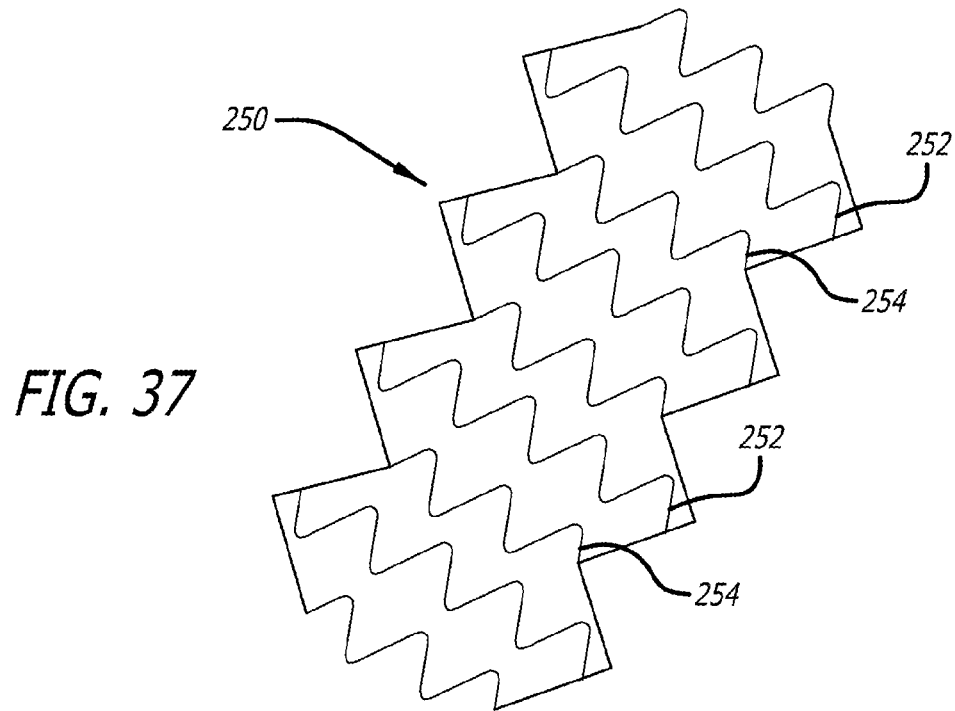

FIG. 37 shows that a stent 250 having a or a corrugated shape, e.g., a "pine cone" profile can be used to secure a stent within a vein. This pine cone shape can be formed by producing a stent with varying ring expansion diameters 252 and 254. The varying stent ring diameter can be accomplished through the use of shape memory metals, e.g. Nitinol, in which the rings are heat set to the desired pine cone shape. Alternatively, a specialized delivery system can be used with a non-cylindrical balloon wherein the balloon has an undulating surface that expands the individual stent rings to varying diameters.

Figure 23:
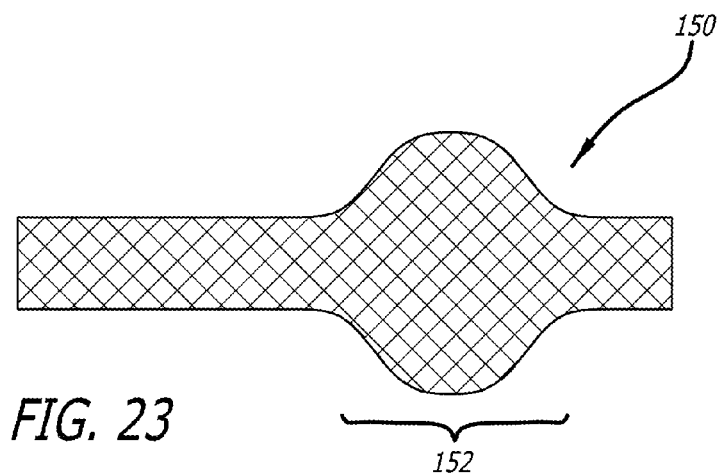
FIG. 23 depicts an intraluminal scaffold having an enlarged non-cylindrical portion according to the disclosed subject matter.

Referring to FIG. 23, a bulbous stent profile is shown. It will be appreciated that one way to expand a bulbous stent 150 is to use a bulbous balloon 154 such as the one shown in FIG.

Figure 24:
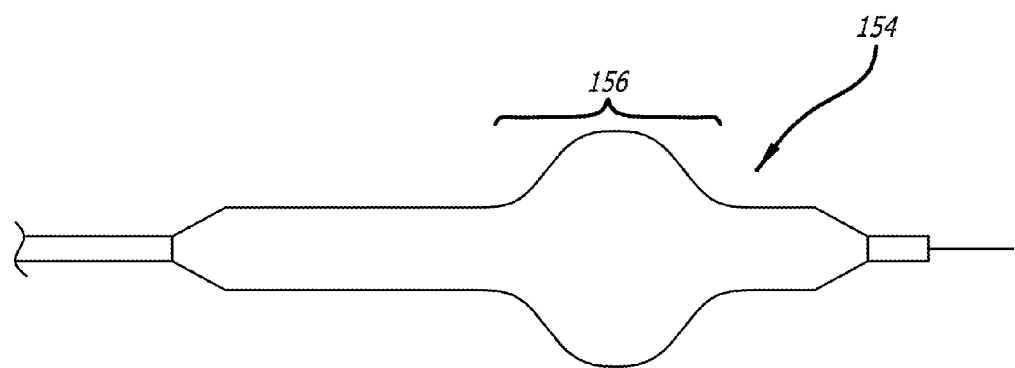
FIG. 24 depicts an exemplary balloon suitable for deploying the stent depicted in FIG. 23.

24. If a balloon such as the one shown in FIG. 24 is used with a deformable stent, it would naturally cause a larger profile in the stent segment that is located over the bulbous balloon section 156. This segment would then provide anchoring within a vein. However, this approach has at least two disadvantages because the production of a bulbous balloon 154 is challenging, given that special molds and processes need to be produced and because molding a balloon in this shape would create an especially weak balloon wall in the bulbous section 156, which is prone to failure. Secondly, even if the bulbous balloon section 156 is successfully formed, it would not necessarily expand the stent 150 in a manner that will conform well to the vessel or produce a beneficial anchoring. This is due to the natural recoil in deformable stents that would be amplified in the case of a non-cylindrical expansion profile.

Figure 25:
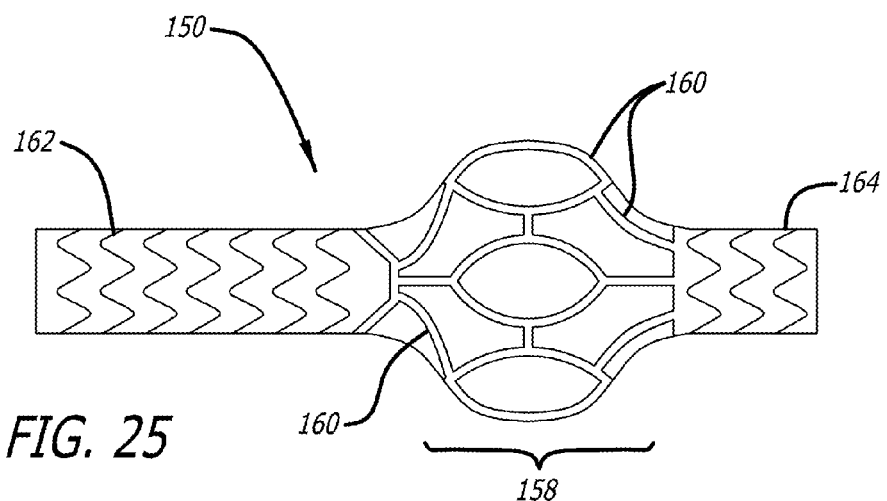
FIGS. 25 through 26 illustrate certain embodiments of an intraluminal scaffold having a bistable construction according to one aspect of the disclosed subject matter.

In some embodiments, the non-cylindrical shaped portion can include a bistable construction. According to this embodiment and referring to FIG. 25, a stent 150 has at least one portion 158 that comprises a bistable stent pattern. This portion 158 is referred to as a bistable portion 158, as it has two stable positions: a low profile position (e.g., a generally cylindrical configuration) and a high profile position. The stent pattern is able to flex between these positions due to the arcuate shaped elements 160 that can bend back and forth with little or no plastic deformation along their length.

Due to the bistable characteristics of the bistable portion 158, it can have an expanded bulbous profile when the arcuate shaped elements 160 are expanded to a significantly larger profile than the expansion diameter of adjacent portions. The adjacent portions 162 and 164 can be conventional meandering stent pattern portions, or any other stent pattern that is of the typical plastically deformable variety. Thus, expansion of the adjacent portions 162 and 164 can be obtained by inflating a balloon rather than on any type of bistable characteristic.

Figure 26:
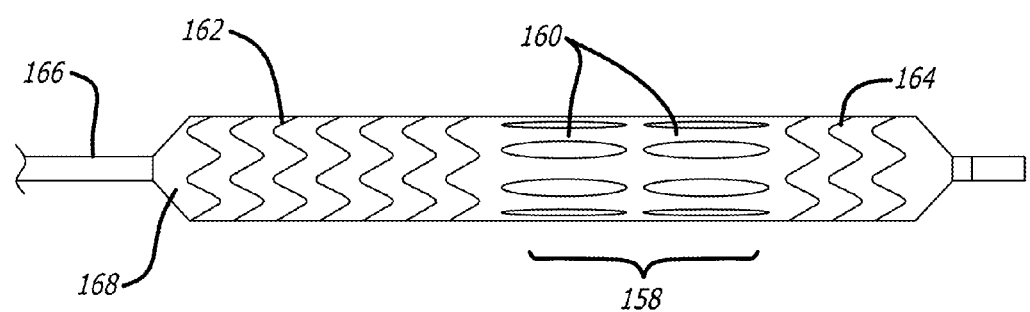

As shown in FIG. 26, the stent 150 can be crimped onto a typical balloon catheter 166 in preparation for delivery. The portions formed from balloon deformable stent patterns can be crimped to a low profile by introducing plastic deformation into the stent struts and crowns. The bistable portion 158 can be crimped to a smaller diameter by forcing the arcuate shaped elements 160 to its low profile configuration. It will be appreciated that much of the bistable portion 158 is not plastically deformed when in this crimped position, but that the bistable portion 158 will nonetheless retain its low profile until it is expanded by a balloon element 168.

Delivery of the stent device 150 into the target vein 170 can be accomplished using standard interventional techniques. The stent delivery system can be tracked over a guidewire (not shown) to the target anatomy, at which point the balloon 168 can be expanded using an inflation medium such as contrast or saline. As the balloon inflates, it will expand the deformable stent portions 162 and 164 against the vessel wall. Likewise, the bistable portion 158 will expand automatically toward a high profile after the arcuate shaped elements are urged past a threshold diameter. Thus, the expansion of the bistable portion 158 will produce a bulbous stent segment with a larger profile without the need for specialized balloon shapes for deployment.

Expansion of the bistable portion 150 can be located within a distended portion of the vessel such that adequate apposition of a distended vessel is achieved. Furthermore, the bistable portion 158 at the expanded configuration can produce an interference with the vessel wall that provides positive anchoring of the stent 150 within the target vessel. The bistable portion can have sufficient flexibility to conform to the distended portion of the vessel without plastic deformation.

The stent having a bistable portion as described above can be fabricated from a number of well known medical device materials. For example, it can be formed from self-expandable materials, e.g. nickel-titanium alloy, plastically deformable materials, e.g. stainless steel or cobalt-chromium alloys, or degradable materials, e.g. PLLA. It will be appreciated that each of these classes of materials encompasses many other materials that would also be suitable.

It is appreciated that although the various embodiments of the stents as described above have been described above as a balloon expandable, they can also be self-expandable or at least in a hybrid variation in which the stent is self-expandable in a selected portion (e.g., the enlarged portion), or have a degree of self-expandable characteristics given that it is fabricated from a self-expanding material, but that its expansion is initially onset by the inflation of a balloon element that it is disposed upon.

In accordance with another aspect of the disclosed subject matter, a method of treating a condition of a vessel is provided. The method includes providing an intraluminal scaffold comprising a generally tubular body with a lumen defined therethrough, the tubular body having a compressed condition for delivery and an expanded condition for implant within a vessel having a distended portion, at least a length of the tubular body configured to form an enlarged portion in the expanded condition; and deploying the scaffold within a distended portion of a vessel with the enlarged portion of the scaffold engaging a wall of the distended portion of the vessel. For example, the enlarged portion can have a non-cylindrical shape. As noted above, various embodiments of the scaffold including an enlarged portion can be used in the method. Additionally or alternatively, the method of treating a condition of vessel includes: providing an intraluminal scaffold comprising a generally tubular body with a lumen defined therethrough, the tubular body having a compressed condition for delivery and an expanded condition for implant within a vessel subject to a valve anomaly; deploying the scaffold within the vessel; and allowing the tubular body of the scaffold to conform to a wall of the vessel. For example, the stent can be formed from a degradable material (e.g., biodegradable, bioabsorbable, or resorbable material) or other polymeric material that will reduce in diameter following expansion for some period of time. The method is useful in situations in which a vein has developed a distension or bulge and there is a desire to allow the vein to return to its original shape or at least to a smaller diameter. In particular, this can be useful in the treatment of CCSVI by mitigating reflux caused by distensions or bulged sections within the internal jugular vein.

Figure 6:
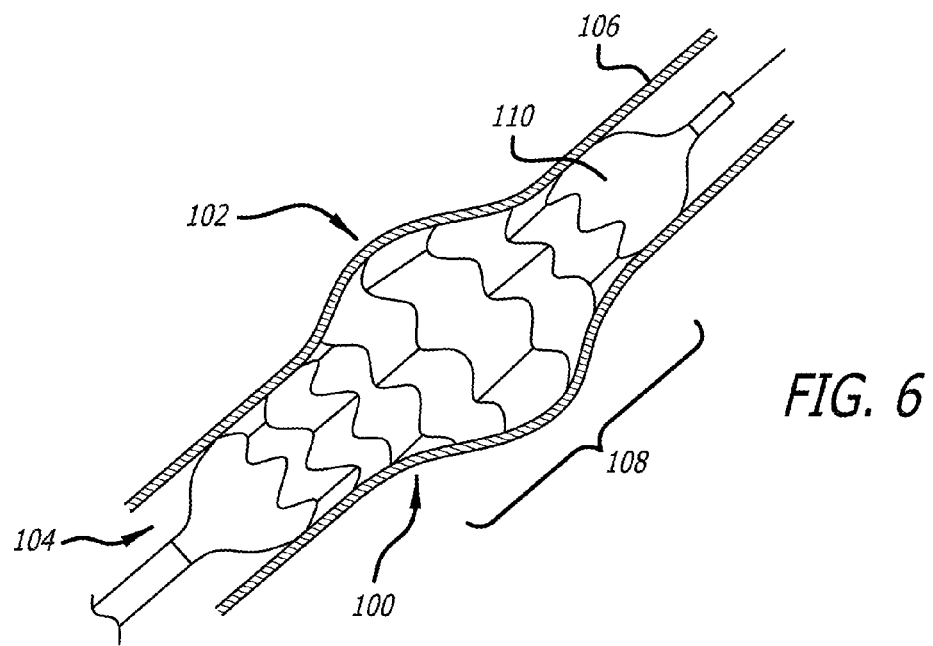

As mentioned above, a vein may be distended or enlarged in any number of shapes that create a risk of blood accumulation and iron deposition; however, for purposes of illustration only the simple bulb shape shown in FIG. 6 will be discussed. In order to treat such a bulb 108, a stent 100 having some amount of natural recoil can be delivered into and engage or conform to the bulb. This expansion can be produced using a medium to high pressure balloon 110 to force the entire vein segment toward a cylindrical configuration, or it can be deployed using an elastic balloon that would be more likely to conform to the shape of the bulb 108.

A certain degree of elastic deformation for the stent 100 during its deployment can be helpful. First, this would allow the stent 100 to conform optimally to the enlarged venous segment. Second, it would encourage the stent to recoil toward its initial shape following deployment into the vessel. A stent formed of a polymer may be suitable for fabricating such a stent due to the ability to tailor the material properties until a desired effect is received. In addition, the stent can be fabricated from a degradable material, which would allow the stent to resorb into the body tissue after the vein is recovered and rehabilitated toward its original condition. Thus, materials such as poly(alpha-hydroxy esters), polylactic acids, polylactides, poly-L-lactide, poly-DL-lactide, poly-L-lactide-co-DL-lactide, polyglycolic acids, polyglycolide, polylactic-co-glycolic acids, polyglycolide-co-lactide, polyglycolide-co-DL-lactide, polyglycolide-co-L-lactide, polyanhydrides, polyanhydride-co-imides, polyesters, polyorthoesters, polycaprolactones, polyanydrides, polyphosphazenes, polyester amides, polyester urethanes, polycarbonates, polytrimethylene carbonates, polyglycolide-co-trimethylene carbonates, poly(PBA-carbonates), polyfumarates, polypropylene fumarate, poly(p-dioxanone), polyhydroxyalkanoates, polyamino acids, poly-L-tyrosines, poly(beta-hydroxybutyrate), polyhydroxybutyrate-hydroxyvaleric acids, combinations thereof, chitosan, PBT, 4-hydroxybutyrate, 3-hydroxybutyrate, or PEG can be used.

Alternatively, the stent 100 can be formed from a deformable or a shape memory material. Although both of these options will provide some remodeling benefit, given that they will both exhibit recoil, it is contemplated that a shape memory material such as Nitinol can be more useful than a deformable material such as stainless steel because it will exhibit greater recoil and thus more pronounced remodeling of the vein.

Figure 7:
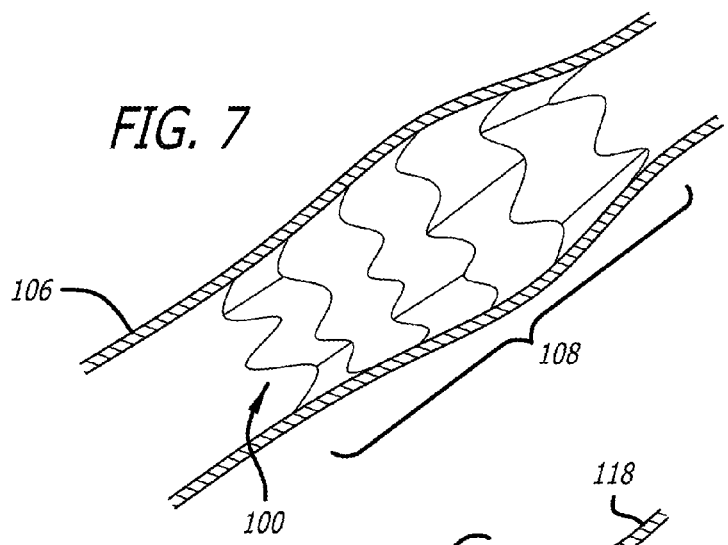

As shown in FIG. 7, after the stent 100 has been expanded within a distended vein 106, it can undergo some amount of recoil, thereby resizing the vein 106 toward a smaller size. In addition to the resilience of the stent material, the recoil can also result from degradation of the degradable material of the stent (if the stent or a portion of the stent is made of such material). The vein 106 will reduce reduce in size as stent 100 undergoes recoil due to the development of adhesion or ingrowth between the stent 100 and the vessel Alternatively, the recoil of the stent can be in response to a reduction in the vessel diameter, e.g., the tubular body of the stent dynamically conforms to the wall of the vessel during vessel relaxation due to adjustments in fluid flow. In either case, the tubular body of the intraluminal scaffold can recoil from its initial expanded condition over a period of time, such as greater than one day.

Figure 8:
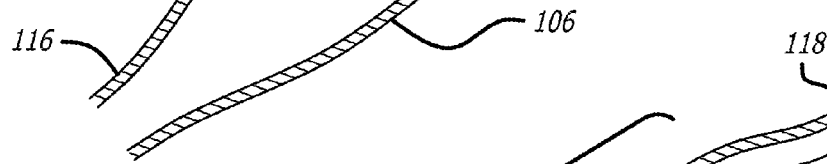
Figure 9:
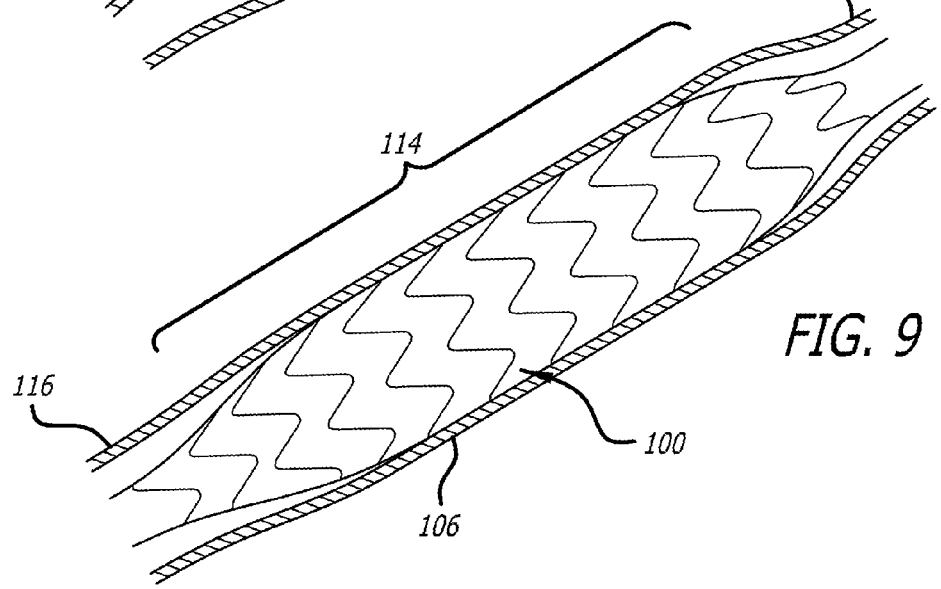

The vein 106 shape may have any number of configurations. For example, it can be distended toward the shape shown in FIG. 8, which essentially creates a vein sac 114 between a proximal bulb segment 116 and distal bulb segment 118 of an internal jugular vein. Therefore, the blood accumulation in this section can contribute to CCSVI and potentially to underlying diseases such as MS. Referring to FIG. 9, a stent 100 can be deployed within the vein segment 114. The vein will adhere to the stent struts and therefore be pulled inward by the stent struts as the entire stent structure undergoes gradual stent recoil. As a result, the vein 106 can be remodeled toward its original shape, which will help mitigate or eliminate the blood accumulation or reflux that is present in the vein.

The degradable material for the stent above can be capable of extravascular degradation. Thus, in the above method, the stent can be allowed to migrate through the vessel wall to be resorbed into the patient anatomy. The remodeled vessel will then be free of foreign bodies and will be restored to its original function. The stent for this embodiment can be formed from a material such as a PLLA, PLGA, and the like.

Figure 18:
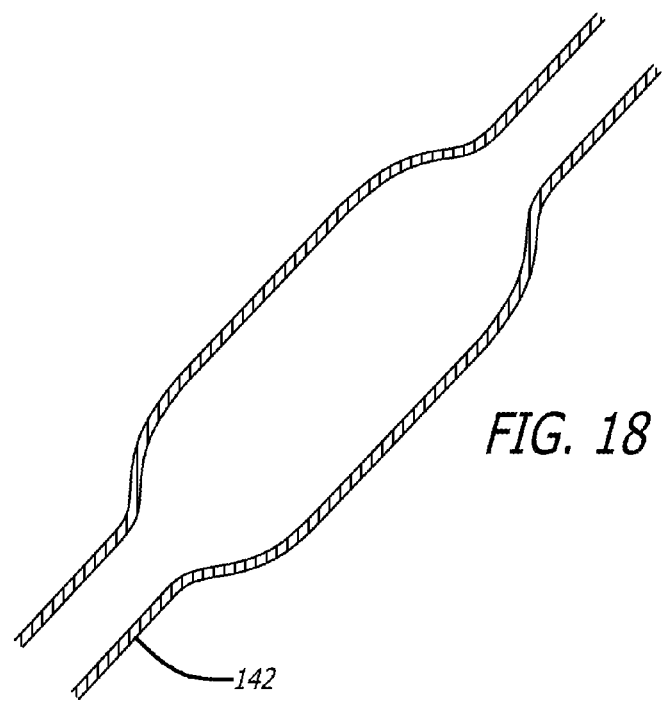
FIGS. 18 through 22 illustrate a method of treating a condition of a vein according to another aspect of the disclosed subject matter.

The stent can be positioned on a balloon catheter and delivered into the target vessel, such as the distended vein 142 shown in FIG. 18. When located at the treatment site, the stent can be expanded and brought into contact with the vessel wall. As appreciated, the stent can have an enlarged portion (e.g., which has a non-cylindrical shape) when expanded as described in any of the various embodiments of the stents as described above.

Figure 19:
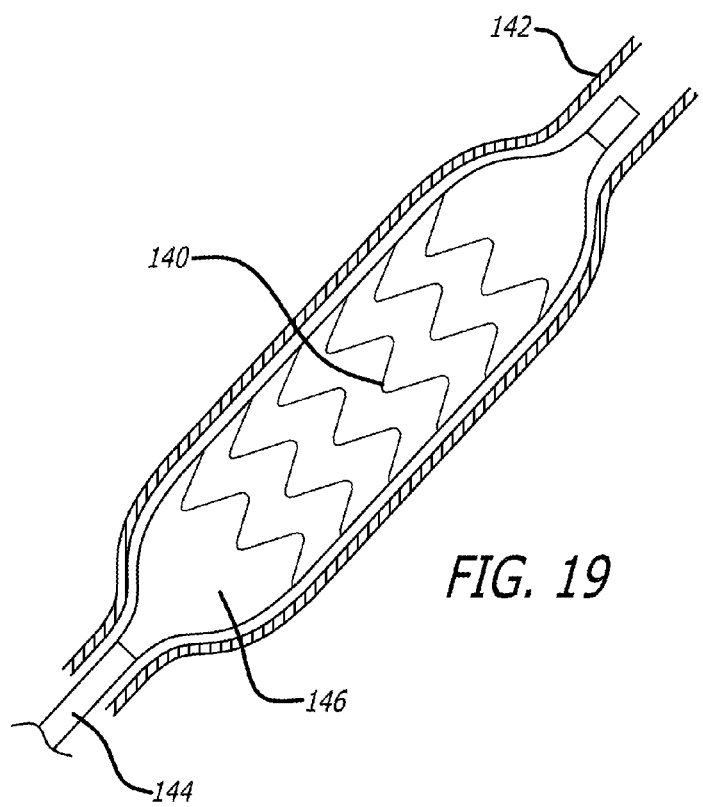

Referring to FIG. 19, the properties of the extravascularly degradable stent 140 are such that it will initially recoil toward a lower profile. When this recoil begins, the stent 140 will have already begun to adhere to, or resorb into, the vessel wall. Thus, a radial inward force will be exerted on the vessel wall and the vessel diameter will reduce along with the stent diameter. As the distended vessel reduces in diameter, it will remodel and result in a smaller diameter vessel. This remodeled shape can help eliminate the reflux that exist in distended veins, thereby have improved function. As shown in FIG. 19, the degradable stent 140 can be delivered to the distended vein 142 using a conventional stent delivery catheter 144 which includes an expandable member, such as an expandable balloon 146.

Figure 20:
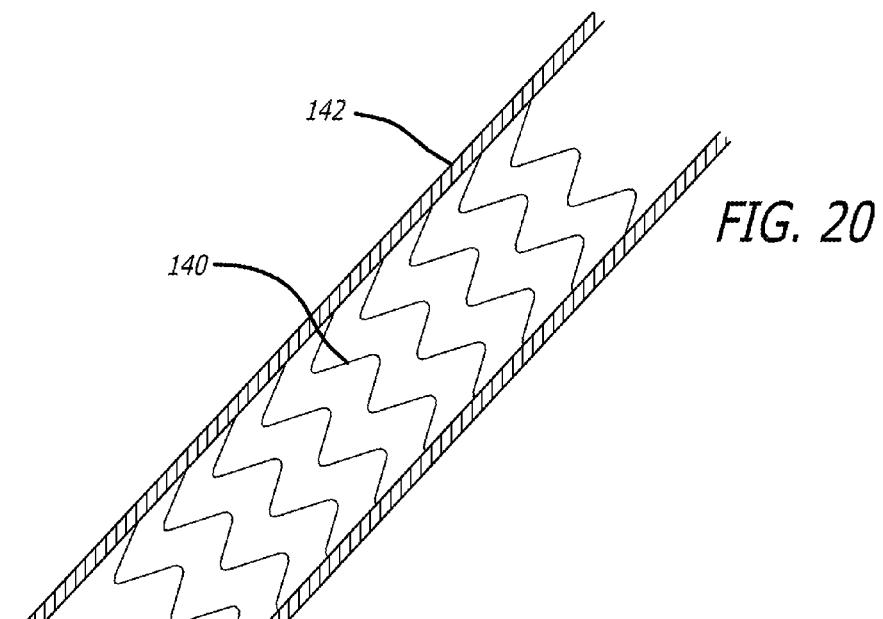

As shown in FIG. 20, as the stent 140 degrades over time and loses much of its radial strength, it will tend to grow outward. This growth will enable the stent to migrate through the venous wall. The phenomenon of stent migration through a venous wall has been confirmed with self-expandable stents. This migration is due to the outward load of the stent and the thin wall of a vein. Since the vein is unable to counteract the outward motion of the stent, it tends to grow around the stent as the stent migrates outward.

Figure 21:
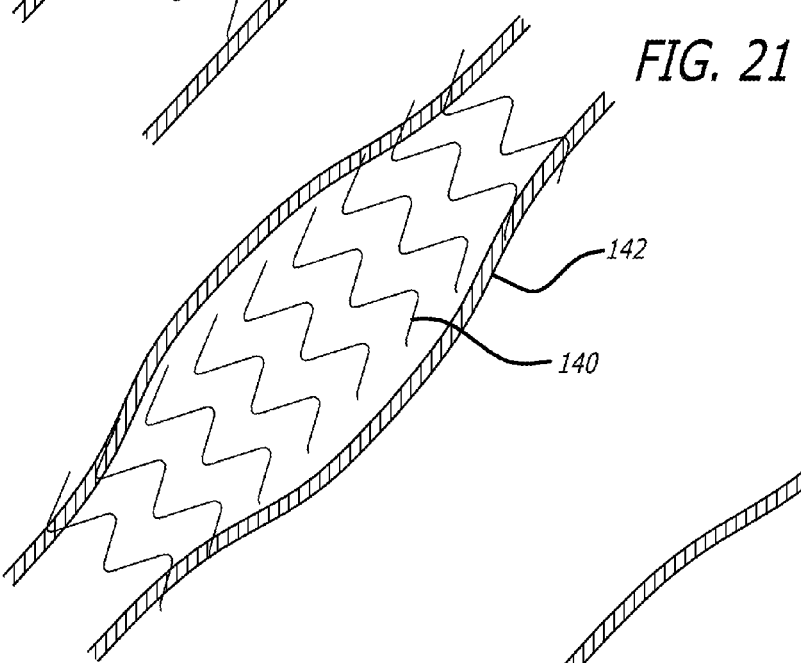
Figure 22:
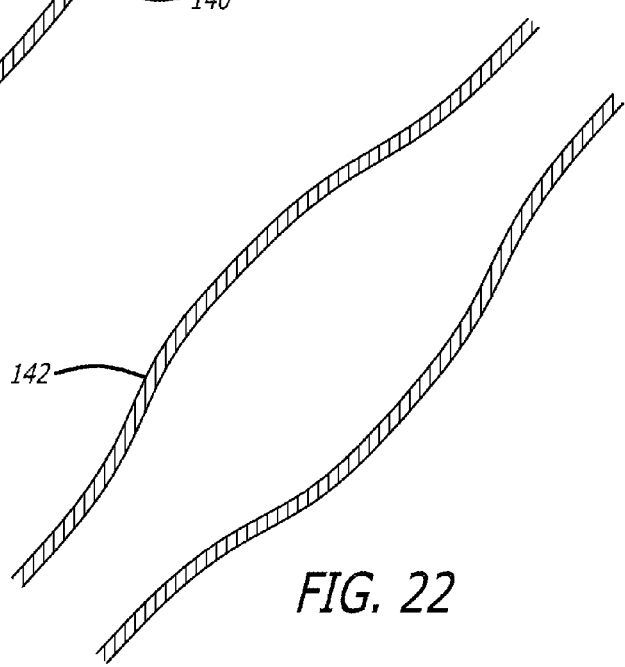

Eventually, the stent 140 will migrate through the venous wall as shown in FIG. 21. Once the stent 140 has traveled into the extravascular space surrounding the vein, it will be able to resorb fully into the patient anatomy as illustrated in FIG. 22. It will be appreciated that in this case the internal surface of the remodeled vein will be completely free of any foreign bodies caused by the stent procedure. Thus, the remodeled vein 142 will exhibit improved function and will be free of flow disturbances or abrupt changes in stiffness that would otherwise be the case in a stented vessel. Furthermore, because there is no stent in the venous wall, there will be reduced risk of vessel injury if the patient is struck in the neck or otherwise physically traumatized in the neck region.

In view of the above, a method is provided herein which includes selecting a patient demonstrating a symptom associated with a condition selected from fatigue, chronic fatigue, venous insufficiency of the leg, chronic venous insufficiency, deep vein thrombosis, Alzheimers, adult onset dementia, Parkinsons, May-Thurner, Budd-Chiari, CCSVI, and MS, and deploying an intraluminal scaffold in a vein having or subject to a valve anomaly believed to be associated with the symptom. For example, the scaffold can be deployed in a vein having one or more valves, such as veins having valves which are atypical or irregular in function or otherwise insufficient. Such valves can be associated with a neck (e.g., jugular), a leg, or a liver, among other things. As a particular example, the vein can be an internal jugular vein.

In accordance with another aspect of the disclosed subject matter, a method for fabricating a scaffold having a non-cylindrical section is provided. The method includes providing a tubular body with a lumen defined therethrough, at least a length of the tubular body configured to form an enlarged portion, and defining a plurality of cells in the tubular body to form an intraluminal scaffold capable of having a compressed condition for delivery and an expanded condition for implant within a vessel, the at least a length of the tubular body having the enlarged portion when in the expanded condition. For example, the enlarged portion can have a non-cylindrical shape.

Figure 10:
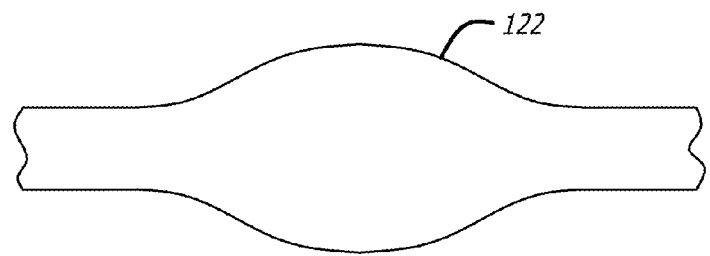
FIGS. 10 through 17 illustrate methods of forming an intraluminal scaffold having an enlarged portion according to a further aspect of the disclosed subject matter.

Referring to FIG. 10, the tubular body, or stent tubing, of a non-cylindrical stent 122 can be used to fabricate the stent 120. The stent tubing can be formed in various manners, such as blow molding, hydroforming, dip molding, and the like, as known in the art. Specific anatomies that may benefit from such a stent 120 include areas with bulges or distended portions, such as those that are common in the bulbous segments of the internal jugular vein. For purpose of examples and not limitation, blow molding can be performed, in which a substantially cylindrical tubing is inserted within a cavity having the desired non-cylindrical form. The tubing is heated and pressurized until the material expands against the cavity walls. Subsequently, the tubing is cooled, allowing it to retain the shape of the cavity. In order to remove the non-cylindrical tubing from the cavity, a split mold design can be used for the cavity. Split mold designs may include one or more seams in the longitudinal or transverse direction. For example, if formed in the longitudinal direction, there may be a split along the length of the mold in two or more locations. Alternatively, if formed in the transverse direction, a single split line can be produced. Alternatively, there may be multiple split lines, in the transverse direction for example, that allow the non-cylindrical form to be compartmentalized. That is, there may be a split line along two shoulders on the tubing, which are spaced apart from each other in the longitudinal direction.

It will be appreciated that the use of a blow molding process may provide structural advantages as well. For example, it is known that the blow molding may produce alignment and orientation of the polymer, which results in improved material strength. By varying the mold design and process, varied strength can be produced throughout the stent tubing. For example, separate portions of the tubing can be blow molded under separate processes so that the amount of stretch, and therefore alignment and material strength can be thereby controlled. Note that blow molding is not the only manner in which a non-cylindrical tubing can be formed. Other processes, such as injection molding, dip molding, extrusion, casting, and any other well-known processes that can form non-cylindrical tubing can also be used.

Figure 11:
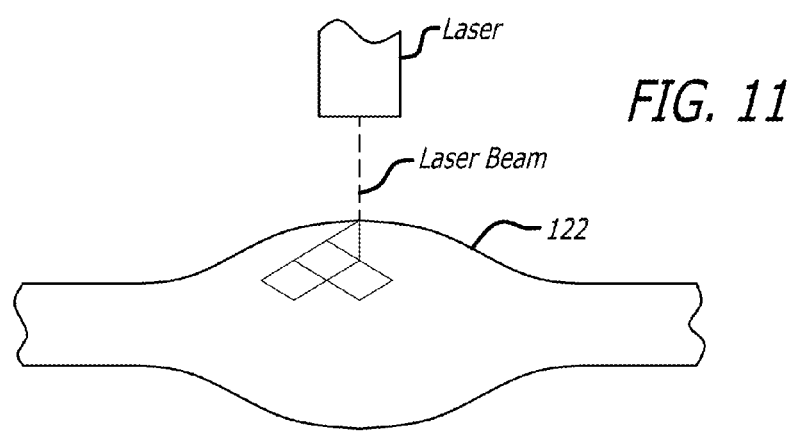

Referring to FIG. 11, after fabrication of the non-cylindrical tubing 122 is complete, a stent structure can be formed from the tubing using a cutting process. It is contemplated that laser cutting of the tubing in a manner traditionally used for stent cutting can be used. It will be understood that adjustments to the process may be made to accomplish this process. For example, the laser head may need to move relative to the tubing surface or other means of maintaining a cutting beam focus at the stent tubing 122 surface will need to be devised to ensure that the stent 120 is properly formed from the tubing. Other methods of forming a stent structure from a tube are known beside the use of laser cutting. For example, micromachining is another suitable method.

Figure 12:
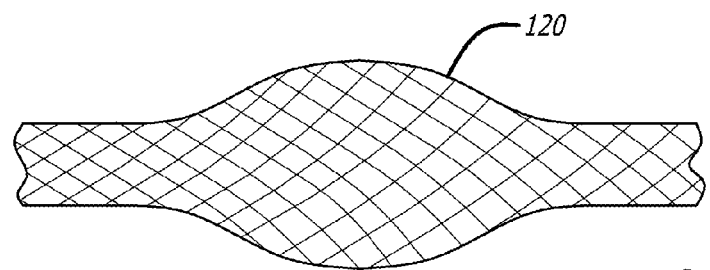

Referring to FIG. 12, a non-cylindrical stent 120 is shown that has been formed from a non-cylindrical tubing. The cell pattern on the stent can be uniform or non-uniform across the stent, as desired. For example, if the stent includes both an enlarged portion and a cylindrical portion, the average cell size of the two portions can be different. Also, the cell pattern on the enlarged portion itself need not be uniform.

In addition to the use of polymeric materials in the formation of this stent 120, such as the use of a degradable polymer stent materials, it is also possible to form a non-cylindrical stent/tubing from a non-polymeric material. For example, the stent tubing 122 can be formed from a deformable metal such as stainless steel or a shape memory metal such as Nitinol. In either case, a specialized process would be required to achieve the non-cylindrical form, which can be achievable through the use of metal forming processes such as forging.

Alternatively, the tubular body can be obtained or prepared by depositing tubular body material, e.g., a metal or metal alloy, on a mandrel having a surface defining the enlarged portion. The deposition can be by vapor deposition, electroplating or any other suitable methods. The material can be deposited across the surface of the mandrel with uniform or varied thickness and then cut as previously described to form the desired cell pattern. Alternatively, the deposition can also be accomplished by depositing the tubular body material on select locations of the surface of the mandrel such that the cell patterns of the stent are established during the deposition.

Figure 13:
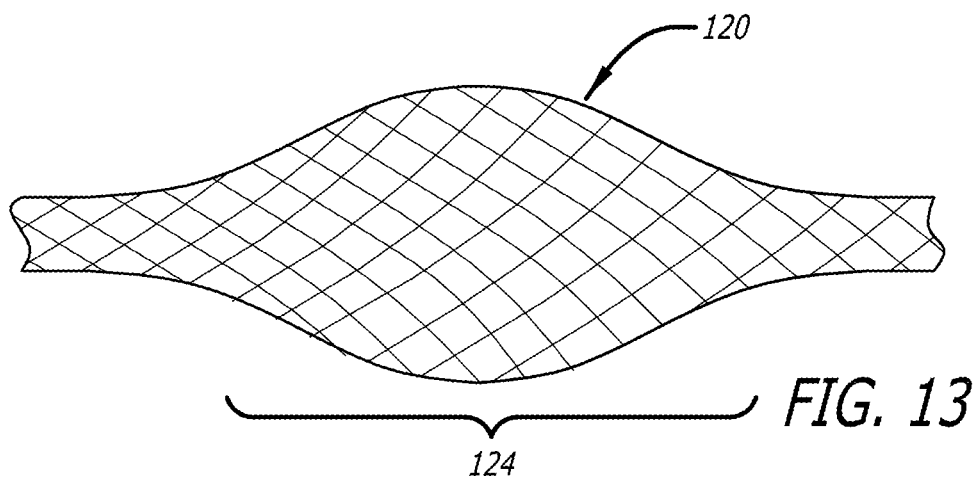
Figure 14:
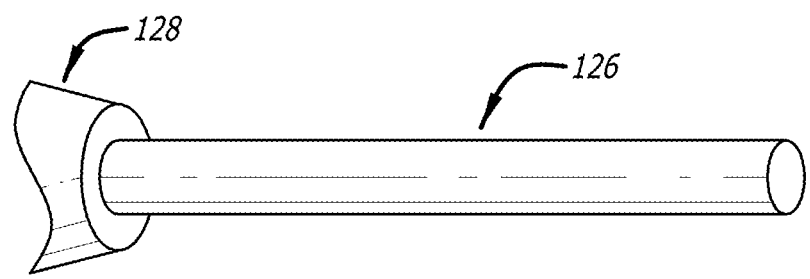

Referring to FIG. 13, a non-cylindrical stent 120 is anticipated to have many useful benefits in the treatment of odd vascular anatomies and in the treatment of veins in general. Hence, the stents disclosed herein can be customized for the desired application. As shown in FIG. 14, a first step in an exemplary process is to produce a cylindrical tube 126 using the material from which a stent will be fabricated. This tube fabrication can be enabled through the use of an extrusion process utilizing exterior equipment 128 as shown, which has been developed and utilized for the creation of polymeric tubing. Alternatively, the tubing 126 could be produced through other well known tubing manufacturing processes such as dip molding or gun-drilling.

In each case, the stent tubing 126 can be formed from a metal, but in the case where degradation or resorption of the stent is desirable, it will more likely be formed from a degradable polymer. Examples of such materials include: poly(alpha-hydroxy esters), polylactic acids, polylactides, poly-L-lactide, poly-DL-lactide, poly-L-lactide-co-DL-lactide, polyglycolic acids, polyglycolide, polylactic-co-glycolic acids, polyglycolide-co-lactide, polyglycolide-co-DL-lactide, polyglycolide-co-L-lactide, polyanhydrides, polyanhydride-co-imides, polyesters, polyorthoesters, polycaprolactones, polyanydrides, polyphosphazenes, polyester amides, polyester urethanes, polycarbonates, polytrimethylene carbonates, polyglycolide-co-trimethylene carbonates, poly (PBA-carbonates), polyfumarates, polypropylene fumarate, poly(p-dioxanone), polyhydroxyalkanoates, polyamino acids, poly-L-tyrosines, poly(beta-hydroxybutyrate), polyhydroxybutyrate-hydroxyvaleric acids, combinations thereof, chitosan, PBT, 4-hydroxybutyrate, 3-hydroxybutyrate, or PEG.

The tubular preform can be opened at one or both ends to permit pressurization of the tubing 126 during the next step of the process. In the case of having both ends open, a temporary seal or plug can be formed with one end 132 when the tubing 126 is pressurized. Alternatively, the tube 126 can be sealed and pressurized from both ends.

Figure 15:
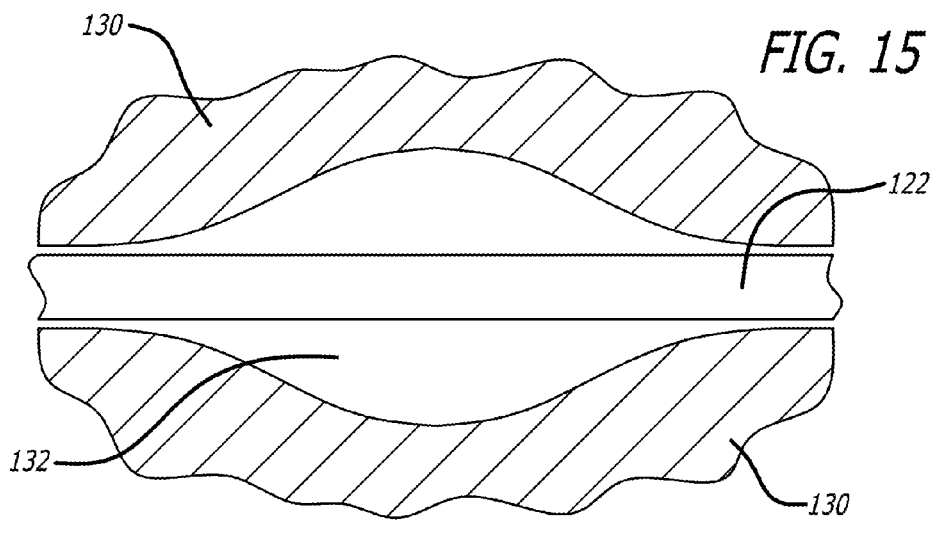

After forming the tube 122, it can be blow molded as shown in FIG. 15. The tube 122 can be inserted within a mold 130 having the form of the desired final tubing shape. In this case, the mold 130 has a bulbous shape 132. The mold 130 can be cooled during the blow molding process. The cooling can be effected through the use of water channels (not shown in FIG. 15) that run through the form, by conductive cooling from a surrounding jacket, or by directing a fluid over the surface of the mold, to name a few possibilities. This cooling is important because it will help to cool the preform after it is formed against the mold surface.

Figure 16:
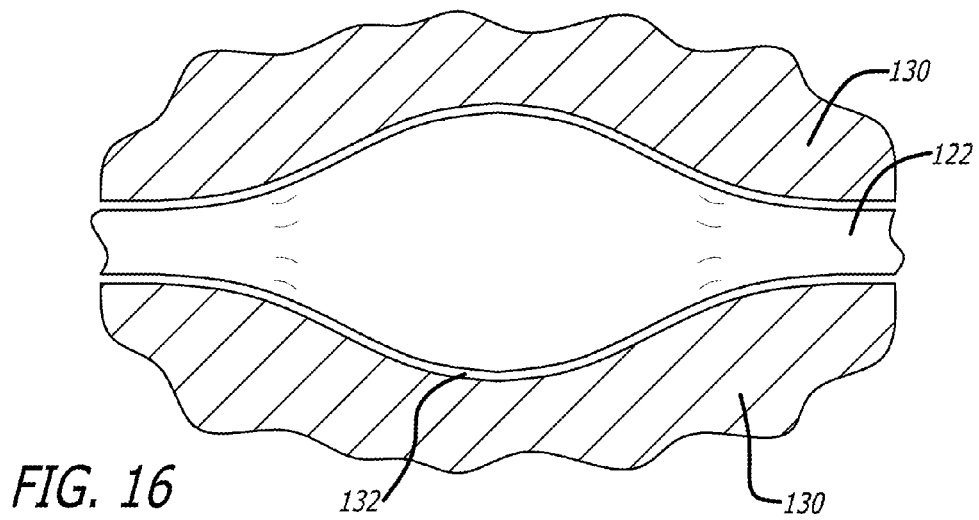

Formation of the tubing form is illustrated in FIG. 16. In one embodiment, the process can be an extrusion blow molding process, such that the tube 122 is extruded concurrently with the blow molding, thus the tube is 122 already heated to an appropriate temperature that will allow it to be deformed when pressurized. Alternatively, the preform can be heated when it is placed within the mold. When the resin is sufficiently heated, the preform is pressurized from at least one end to cause the entire preform to expand outward toward the surface of the mold cavity 132. Once the preform contacts the mold cavity, it will be cooled by the mold surface, and tubing will solidify in its final form. The part can then be ejected in its final form.

It will be appreciated that there are many different methods of blow molding plastic components, and that the method of manufacturing stent tubing described herein is intended to encompass all of these. For example, in addition to extrusion blow molding, it is also possible to use injection blow molding and stretch blow molding. Furthermore, variations of these processes are possible, including continuous extrusion blow molding, intermittent blow molding, and many other variations that one skilled in the art could employ to form a non-cylindrical tubing that is suitable for manufacturing a stent device.

Figure 17:
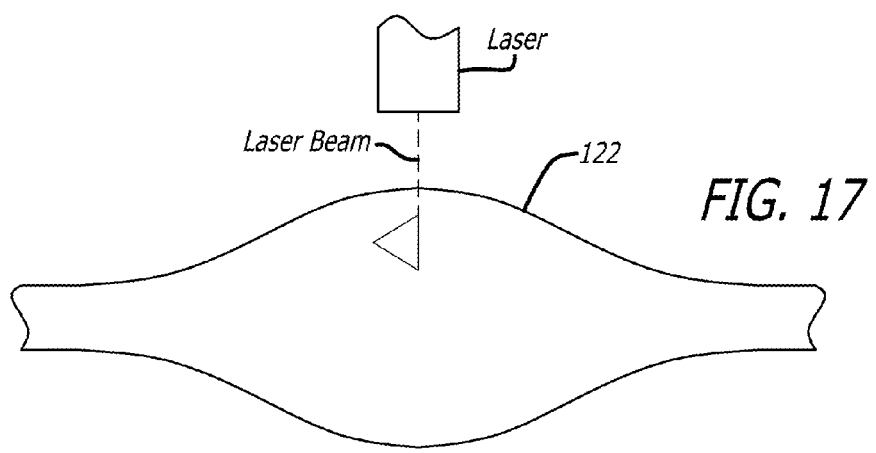

After formation of the non-cylindrical stent tubing using the process described above, the tubing 122 may then be used to form a stent structure. As shown in FIG. 17, a laser can be directed toward the tubing surface to cut the desired pattern into the tubing structure 122. This step may require specialized laser technologies that will allow for cutting of a non-tubular surface. For example, either the position of both the laser source or the stent tubing can be maintained while adjusting the focal point of the laser in the z-direction. Alternatively, one or both of the laser source or the stent tubing can be adjusted along the z-direction in order to ensure that the focal point of the laser impinges on the tubing surface. Furthermore, the angle of either the laser source or the tubing axis can be changed in order to ensure that the laser beam impinges basically perpendicular to the tubing surface at all times.

After the stent structure 120 has been cut into the non-cylindrical tubular component, subsequent manufacturing processes can be performed. For example, there can be subsequent polishing steps to remove islands or burrs from the stent struts. Additionally, there may be crimping processes required to reduce the stent diameter in order to mate with a deployment balloon or a delivery sheath. These additional processes can be developed as required or desired.

The stent can then be crimped and loaded over the balloon component of a balloon delivery system. Alternatively, the stent can be crimped and loaded into a delivery system sheath. The stent delivery system can then be advanced through the patient anatomy to deploy the stent at a target patient location. This deployment can be performed in a manner that is commonly used for stent delivery systems, such as inflation of a balloon component that expands the stent or retrieval of a sheath that allows the stent to self-expand to a final configuration.

In accordance with another aspect of the present application, a stent is provided which includes a first annular element radially expandable with respect to a longitudinal axis defined therethrough, a second annular element radially expandable with respect to the longitudinal axis, and at least one axial strut connecting the first annular element and the second annular element, the at least one axial strut having sufficient flexibility to conform to a wall of a distended portion of a vessel.

Figure 38:
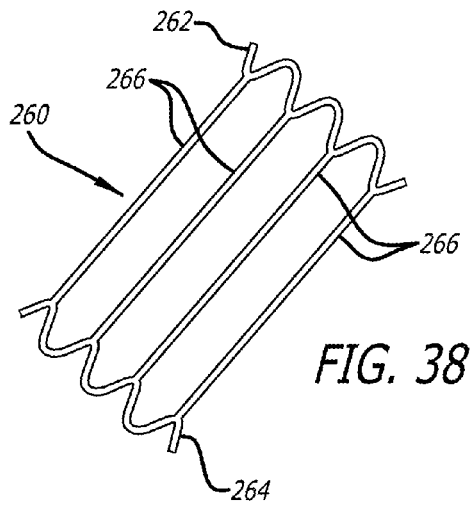
FIGS. 38 through 41 illustrate various embodiments of an intraluminal scaffold having one or more generally axial struts according to another aspect of the disclosed subject matter.

Referring to FIG. 38, in an embodiment stent 260, a stent with a distal ring 262 and a proximal ring 264 (flattened view) having a generally meandering configuration as is well known in the stent art are connected by one or more axial struts 266. These axial struts 266 have relatively low radial strength and high flexibility in comparison to meandering struts. In a way, the axial struts act as end-supported beams with high spans. Thus, the axial struts can have sufficient flexibility to avoid forcing the venous wall outward excessively, and to conform to a distended portion, e.g., a non-cylindrical vessel wall.

Figure 39:
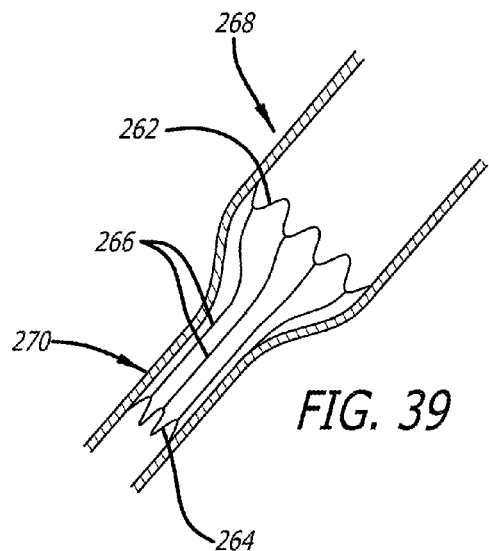

As shown in FIG. 39, such a stent 260 can be used to treat the bulbous portion 268 of the internal jugular vein. The meandering stent rings can be expanded to the diameter of the vein portions they were respectively implanted, i.e. either within the proximal small diameter portion 270 or the distal bulbous portion 268. The axial struts 266 spanning these rings 262 and 264 will conform to the tapered vessel wall.

It will be appreciated that although not shown, the vessel can eventually remodel to a smaller size that is more cylindrical. For example, in a case in which the stent is expanded across a bulge wherein the axial struts support the bulge and the meandering stent rings are placed on either side of the bulge, it is possible that the venous wall would adhere to the axial struts. Thus, over time the axial struts can reduce in profile as they retract to their original shape, and this would cause the vein to remodel along with the struts.

Figure 40:
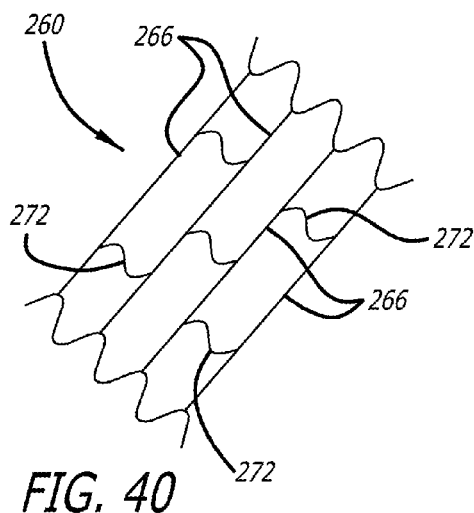

As shown in FIG. 40, the flexibility and strength of the axial struts 266 can be controlled by using additional radial connectors 272 features that provide radial stability and control the unsupported span length of the axial struts. These radial connectors 272 will provide radial support as well. The location of the connectors 272 can be manipulated to achieve the desirable flexibility or radial strength. In general, the more radial connectors 272 present, the stiffer the stent structure will be.

Figure 41:
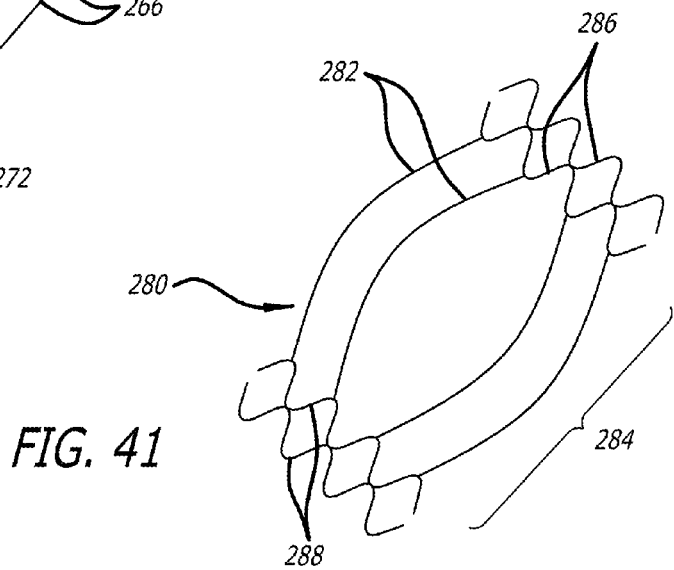

In still another embodiment, as shown in FIG. 41, a stent 280 can be formed with axial struts 282 forming a bulbous portion 284. This can be accomplished in one way by cutting the stent from a non-cylindrical tube. Alternatively, the bulbous shape of the struts can be achieved by deploying the stent 280 with a bulbous balloon that forces the axial struts outward into the arcuate configuration. One or more end rings 286 and 288 can be attached to the axial struts 282. This can be accomplished, for example, with a secondary balloon that is deployed into the stent after the initial stent expansion.

This stent can be formed from multiple material types, including metals and polymers of all types. Further, different portion of the stent can be formed of different materials. For example, the stent can includes a hybrid structure in which one or more end rings (266 and 288) are formed from a balloon expandable stent structure. These balloon expandable structures are preferably fabricated from materials such as stainless steel or cobalt chromium, which are able to plastically strain in order to reset the stent structure to a larger diameter. The structure itself can be designed to accommodate a large range of diameters. For example, it can be expanded to a range of between about 5 mm and 20 mm with sufficient radial strength to ensure that the stent can prop open a venous structure. In comparison, the scaffold struts 282 can be formed from a self-expandable material. For example, the struts can be formed from a nickel-titanium alloy such as nitinol. In this way, the struts can be formed in an arcuate shape. In the case of a bulging vessel, this will result in a stent that closely conforms to the bulge. In the case of a non-bulging vessel or one in which the struts are placed across the stenosed venous valves, the arcuate struts will provide higher radial strength and ensure that the valves remain open.

Various bonding processes can be used to associate the end rings and arcuate strut segments. For example, thermal welding can be used to bond the components. Alternatively, the components can be bonded with adhesive. Also, the components can be associated through mechanical means such as by tying them together with a third component, e.g. suture. Alternatively, both the end rings and the axial struts can be formed a self-expandable material, such as nitinol stent. Nitinol can be formed in either an austenitic or martensitic phase. In the austenitic phase, the nitinol exhibits the shape-memory characteristics mentioned above. However, when the nitinol is in the martensitic phase, it behaves in a plastically deformable manner, and thus can be used to form a stent ring that is balloon expandable. Therefore, the end rings can be formed from nitinol in its martensitic state and the arcuate strut segments can be formed from nitinol in its austenitic state.

An all-nitinol stent structure is advantageous in at least two ways. First, the thermal welding of nitinol to nitinol can be performed more easily than the process of bonding nitinol to a dissimilar material. In addition, a stent formed from a single material is less likely to encounter galvanic effects that occur between dissimilar materials, and this will make the stent less susceptible to in-vivo corrosion.

Deployment of a hybrid stent as above can be performed using a balloon and/or a balloon-sheath combination. In the case of a balloon catheter, the stent can be crimped on the balloon element in a manner typical of balloon expandable stents. During the crimping process, the stent can be stretched such that the arcuate segments straighten and conform to the balloon profile. The struts will remain straightened due to the frictional securement between the end rings and the balloon element. Alternatively, a sheath can be used in combination with the balloon element to ensure that the struts remain in a low profile. In this case, the sheath is placed over the crimped stent to resist any tendency of the struts to bow outward during device delivery.

A stent of this type can be deployed in a manner that promotes conformance to the vessel wall. For example, the proximal and/or distal end of the stent can be deployed prior to the opposing end of the stent. Thus, a single ring can be deployed at a time. By doing this, when one ring is deployed it will allow the arcuate struts to expand wholly or partially. Therefore, the arcuate struts will conform closely to the vessel near the deployed end ring. When the second end ring is deployed, the struts will be able to gradually deploy into the vessel simultaneously. This reduces the risk that the struts can be stretched or bunched during simultaneous expansion of the end rings. Therefore, overall conformance to the vessel can be improved. In order to facilitate this type of expansion, there may be a benefit in using a multi-balloon system. Therefore, one balloon will engage each end separately, allowing the ends to be deployed separately. Alternatively, a single balloon can be used, however a sheath can be placed over the stent and retracted as desired to allow one ring to be exposed to the vessel while the other ring is covered. The exposed ring can therefore be expanded by inflating the single balloon. After expanding one ring, the sheath can be retracted further to expose the second ring and that ring can be deployed by additional balloon inflation.

Further still, it is contemplated as disclosed herein that the stent can be formed of multiple independent ring sections of varying sizes. The independent rings can be that are separately deployed in the vessel, whereby certain locations along the vein receive a ring section with a first radial diameter and the other locations along the vein receive a ring section of a second radial diameter greater than that of the other sections.

In accordance with another aspect of the disclosed subject matter, the stents or scaffolds as described herein further include a drug or therapeutic substance selected from those described below for treating, ameliorating, or inhibiting a condition of concern of a patient. The therapeutic substance can be coated on the scaffold or otherwise incorporated. For example, the therapeutic substance can be included in reservoirs formed on the surface of the scaffold, or impregnated in a coating of a polymer layer coated on the scaffold.

Therapeutic substances as used herein include biologically active agents and can be, for example, therapeutic, prophylactic, or diagnostic agents. As used in this document, the therapeutic substance includes a bioactive moiety, derivative, or metabolite of the therapeutic substance.

Examples of suitable therapeutic and prophylactic agents include synthetic inorganic and organic compounds, proteins and peptides, polysaccharides and other sugars, lipids, and DNA and RNA nucleic acid sequences having therapeutic, prophylactic, or diagnostic activities. Nucleic acid sequences include genes, antisense molecules, which bind to complementary DNA to inhibit transcription, and ribozymes. Other examples of therapeutic substances include antibodies, receptor ligands, and enzymes, adhesion peptides, oligosaccharides, blood clotting factors, inhibitors or clot dissolving agents, such as streptokinase and tissue plasminogen activator, antigens for immunization, hormones and growth factors, oligonucleotides such as antisense oligonucleotides and ribozymes and retroviral vectors for use in gene therapy.

In other examples, the drugs or therapeutic substances inhibit vascular-smooth-muscle-cell activity. More specifically, the therapeutic substance may inhibit abnormal or inappropriate migration or proliferation of smooth muscle cells leading to restenosis inhibition. Therapeutic substances can also include any substance capable of exerting a therapeutic or prophylactic effect. For example, the therapeutic substance could be a prohealing drug that imparts a benign neointimal response characterized by controlled proliferation of smooth muscle cells and controlled deposition of extracellular matrix with complete luminal coverage by phenotypically functional (similar to uninjured, healthy intima) and morphologically normal (similar to uninjured, healthy intima) endothelial cells.

The therapeutic substance can also fall under the genus of antineoplastic, cytostatic or anti-proliferative, anti-inflammatory, antiplatelet, anticoagulant, antifibrin, antithrombin, antimitotic, antibiotic, antiallergic and antioxidant substances.

Antineoplastic or Antimitotic Examples:
paclitaxel
docetaxel
methotrexate
Azathioprine
Vincristine
Vinblastine
Fluorouracil
doxorubicin hydrochloride
mitomycin
Antiplatelet, Anticoagulant, Antifibrin, and Antithrombin Examples:
Heparinoids
Hirudin
Argatroban
Forskolin
Vapiprost
Prostacyclin
prostacyclin analogues
Dextran D-phe-pro-arg-chloromethylketone (synthetic antithrombin)
Dipyridamole
glycoprotein IIb/IIIa platelet membrane receptor antagonist antibody
recombinant hirudin and thrombin inhibitors
Cytostatic or Antiproliferative Agent Examples
Angiopeptin
angiotensin converting enzyme inhibitors
cilazapril
lisinopril
actinomycin D
dactinomycin
actinomycin IV
actinomycin $I_1$
actinomycin $X_1$
actinomycin $C_1$
actinomycin D derivatives or analogs
Other Therapeutic Substances Include
calcium channel blockers
nifedipine
Colchicines
fibroblast growth factor (FGF) antagonists
omega 3-fatty acid
Fish oil
Flax seed oil
histamine antagonists
lovastatin
monoclonal antibodies (such as those specific for Platelet-Derived Growth Factor (PDGF) receptors)
Nitroprusside
phosphodiesterase inhibitors
prostaglandin inhibitors
Suramin
serotonin blockers
Steroids
thioprotease inhibitors
triazolopyrimidine (a PDGF antagonist)
nitric oxide
alpha-interferon
genetically engineered epithelial cells
antibodies such as CD-34 antibody
abciximab (REOPRO)
progenitor cell capturing antibody
pro-healing therapeutic substances (that promotes controlled proliferation of muscle cells with a normal and physiologically benign composition and synthesis product)
Enzymes
anti-inflammatory agents
Antivirals
anticancer drugs
anticoagulant agents
free radical scavengers
Estradiol
steroidal anti-inflammatory agents
non-steroidal anti-inflammatory
dexamethasone
clobetasol
aspirin
Antibiotics
nitric oxide donors
super oxide dismutases
super oxide dismutase mimics
4-amino-2,2,6,6-tetramethylpiperidine-1-oxyl (4amino-TEMPO)
Tacrolimus
Rapamycin
rapamycin derivatives 40-O-(2-hydroxy)ethylrapamycin (everolimus)
40-O-(3-hydroxy)propyl-rapamycin
40-O-[2-(2-hydroxy)ethoxy]ethyl-rapamycin
40-O-tetrazole-rapamycin
Zotarolimus™
cytostatic agents
Antiallergic Agent Such as Permirolast Potassium.

In particular embodiments, the therapeutic substance can include one or more of fondaparinux (Arixtra®), Enoxaparin, Bivaliruden, a factor Xa inhibitor, a collagenase (e.g., Xiaflex®), and endopeptidase.

In a further aspect, the disclosed subject matter also provides methods and devices for deploying a medical device. The method includes establishing an open condition of a valve in a vessel of a patient, moving a medical device through the opened valve; and deploying the medical device at a target site. Each of the operations above is completed without negatively impacting the function of the valve. The methods herein can be used in any vessel having one or more valves. For purpose of illustration, reference will be made to a venous system below.

The medical device to be deployed can be any of the scaffolds as described above, as well as other treatment devices such as surgical devices, balloons, implants, grafts, or the like. The method allows for minimization of trauma to the venous valves. By reducing trauma to the valves, a stent, balloon, or other medical device can be used to treat a venous condition, e.g., venous insufficiency, while minimizing damage that could be counterproductive to the goals of the vein treatment.

Figure 50:
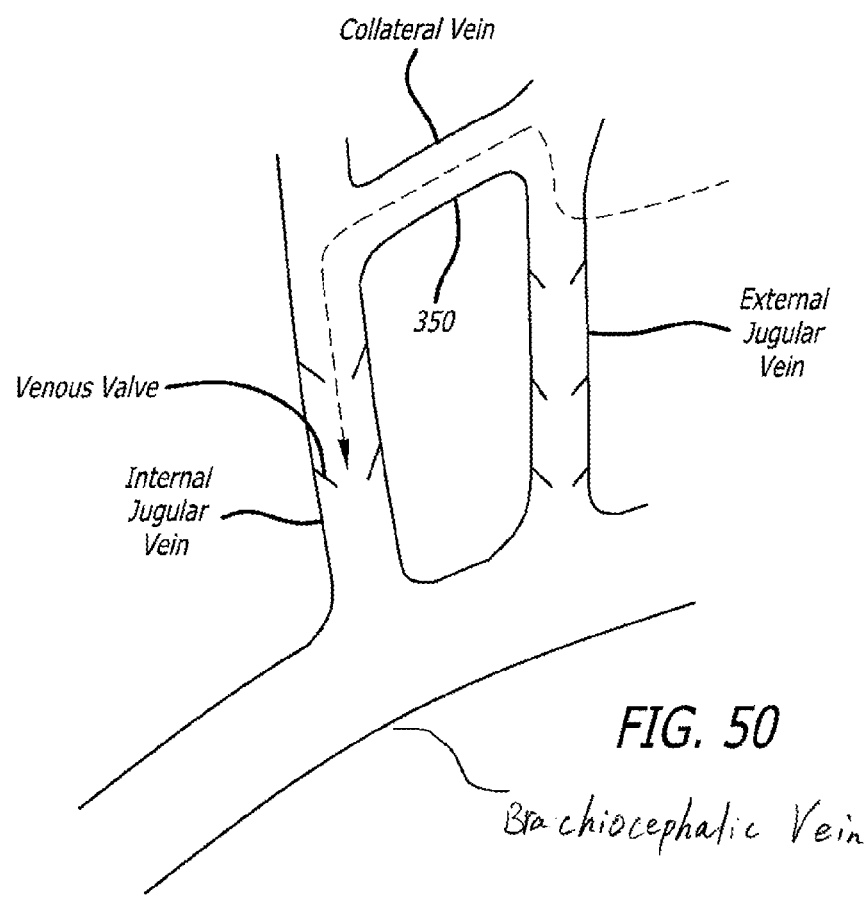
FIGS. 50 through 51 illustrate a method of accessing veins through the neck according to one embodiment of the disclosed subject matter.
Figure 51:
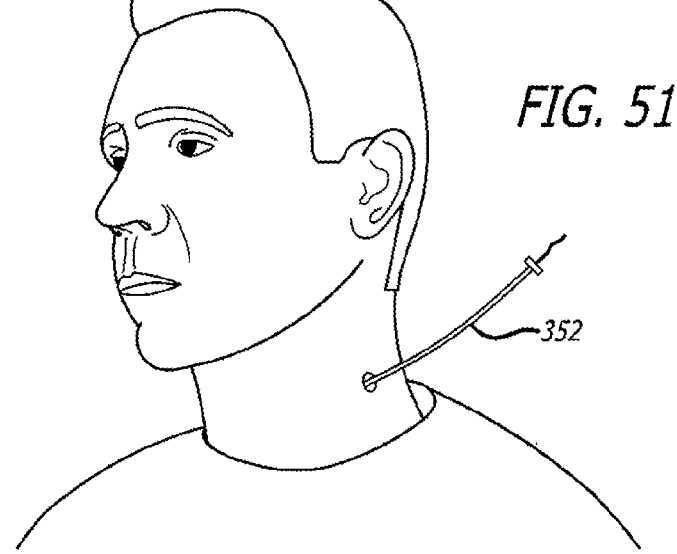

One exemplary target site is an internal jugular vein as discussed above, the distension of which is associated with the conditions of CCSVI and can be treated by employing the various embodiments of stents as described above. To access a target site in an internal jugular, a vascular access device such as an introducer sheath can be introduced via the external jugular, e.g., via an access path (depicted by the broken line 350 in FIG. 50) as shown in FIG. 50. Thus, the access device can be tracked through collateral veins stemming from the external jugular vein into the descending internal jugular vein. As these devices will be traveling in the antegrade direction, there will be minimal risk of valve damage during their delivery. FIG. 51 illustrates how this access can be made in a patient's neck. The introducer sheath 352 can be inserted using well known techniques similar to those used to gain access to a patient's femoral or radial arteries. This can be accomplished through the initial introduction of an introducer needle and a guidewire, and the subsequent exchange of an introducer sheath for the introducer needle. Thus, a route of access is gained within the venous anatomy and guidewires or devices can be delivered into the veins as needed.

Referring back to FIG. 50, it will be appreciated that the pathway through the network of veins and arriving at the target location may vary depending on the circumstances of individual cases. A variety of independent collateral veins exist that interconnect the jugular veins in the venous network, and therefore a medical device can be inserted and tracked through any of these veins to reach the desired destination. However, it will be appreciated that under all circumstances, this method prefers that the device will be tracked through each of these veins in an antegrade direction whenever possible. The external jugular vein is anticipated to be a useful site of introduction because it is covered by comparatively less tissue relative to the internal jugular vein and perhaps as compared to other collaterals as well. Therefore, introduction into the external jugular vein should be easier to visualize, easier to achieve, and should also cause less tissue trauma as compared to other access points. Nonetheless, although the external jugular vein is a preferred access site given its relative size and location, other veins can be used for access to the internal jugular vein as well. In an alternative embodiment, access to the internal jugular vein can be made directly, or access can be made into one of the collateral veins other than the external jugular vein.

Figure 42:
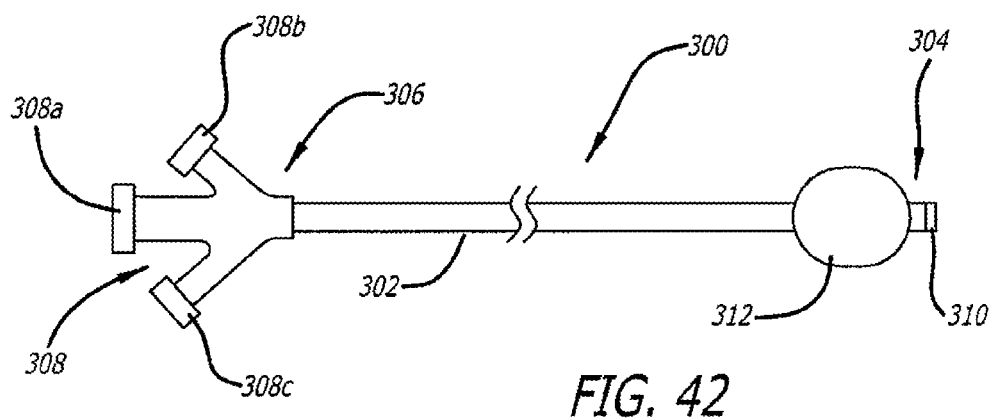
FIGS. 42 through 44 schematically illustrate a catheter device and an associated method suitable for deploying a medical device across a valve according to one aspect of the disclosed subject matter.

Establishing an open configuration of the valve can, for example, includes altering fluid flow in the vicinity of the valve, as well as other approaches as further explained below. In one embodiment, the method includes drawing blood flow in an antegrade direction, e.g., by using suction, thereby opening the venous valves. While the venous valve is opened, a guidewire or other treatment device can be advanced through the valve in a retrograde direction using a delivery device. The treatment device thus can be delivered without damaging (e.g., tearing or snagging) the leaflets. After deploying the medical device, the delivery device, such as a catheter, can be retrieved or removed. Alternatively or additionally, the medical device can also be retrieved or removed while the valve is in an open position, or the medical device can be implanted and remain Referring to FIG. 42, an exemplary embodiment of a device is shown. The device 300 comprises an elongated catheter body 302 having a distal portion 304 and a proximal portion 306. The proximal portion 306 can include one or more ports 308 for communicating with the distal catheter end 304. For example, one port can be a device port 308a, which allows a medical device such as a guidewire (see FIG. 44) to be advanced through the port into a lumen that runs the length of the catheter body 302. The medical device can be advanced through the device port 308a and catheter lumen to exit the distal end 310 of the catheter device. In addition, there may be an inflation port 308b near the proximal end that allows for an inflation fluid to communicate with the distal catheter portion 304 through an inflation lumen disposed within the catheter body.

The distal portion 304 of the catheter can include an occlusion balloon 312. This balloon 312 is can be formed from a compliant material, such as an elastomeric material. The balloon 312 is placed in communication with the inflation lumen of the catheter body, such that introduction of an inflation fluid through the inflation port 308b will cause the balloon 312 to expand. When positioned within a body vessel, expansion of the balloon 312 can cause the vessel to be occluded.

In addition, a suction port 308c can be positioned near the proximal portion 306. This suction port 308c can communicate with a suction lumen disposed within the catheter body. The suction port 308c can have a vacuum applied to it by attached a syringe (not shown) to the port connector 308c and drawing a vacuum within the syringe. It will be appreciated that doing so while the catheter is located within a vein will cause blood to be drawn through the suction lumen into the syringe.

Figure 43:
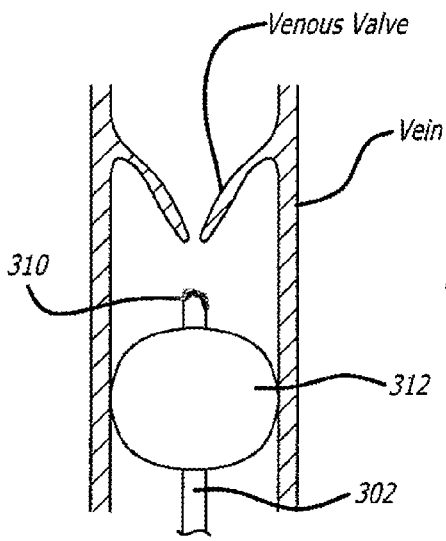

A method of using the device to draw a suction within a patient anatomy is shown in FIG. 43. The device can be advanced through the patient anatomy until the distal end is located near and downstream of a venous valve. The occlusion balloon that is disposed near the distal end of the device can be expanded by introducing an inflation fluid through the inflation port. As the balloon expands, it will contact the vessel wall and form a seal in the vessel, which prevents the antegrade flow of blood.

Figure 44:
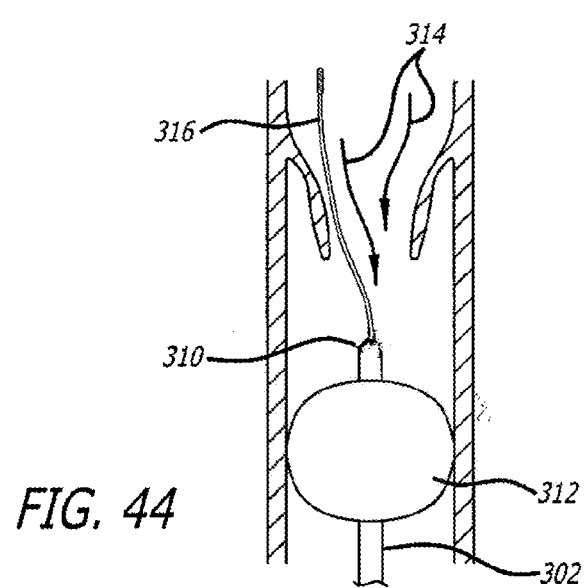

As shown in FIG. 44, when the vessel is occluded, a suction can be drawn through the suction port using a syringe or another apparatus that can produce a vacuum. The suction will result in the increased flow of blood in the antegrade direction as the blood enters the suction lumen of the catheter and is drawn into the syringe near the proximal end of the device. While this suction is produced, the valves of the vein will tend to open due to the continuous antegrade blood flow depicted by arrows 314 or FIG. 44. During this time when the valves are opened, a guidewire 316 or another device can be advanced through the device lumen into the vein in a retrograde direction. The device 316 can advance freely through the valves because they will be dilated such that the passage of the device 316 is less likely to snag on the valve, or if it does, is more likely to deflect away and move through the vessel.

The method of drawing suction and advancing a device to cross through a valve without damaging it can be performed repeatedly in an intermittent fashion. For example, suction can be drawn at each point when the device is adjacent to, and ready to cross through, a valve. Alternatively, suction can be drawn continuously the entire time that the device is being advanced through the vessel.

After a guidewire 316 is placed through the length of vessel that is intended to be treated, a medical device such as a stent or balloon catheter can be advanced over the guidewire and through the vessel length including the venous valves to the treatment site. This delivery can be aided through the use of suction as described above, as well. In this case, depending on the size of the medical device, a suction catheter of appropriate size and configuration can be used to accommodate the size and configuration of the medical device.

Figure 45:
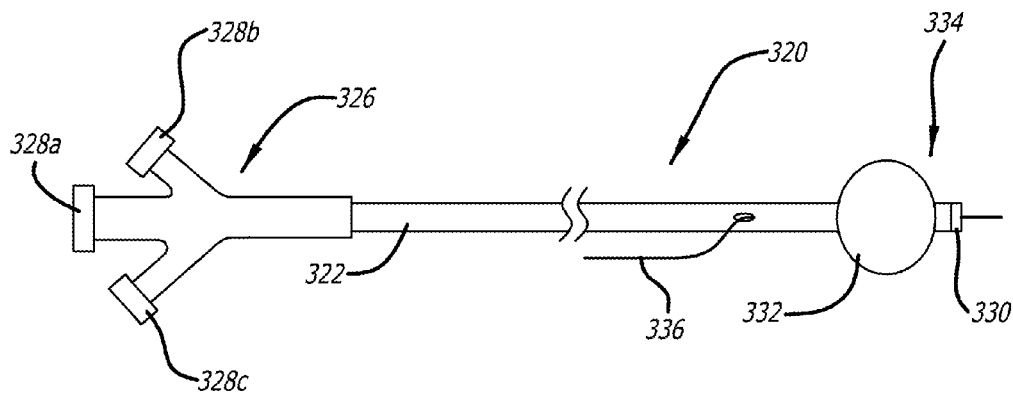
FIGS. 45 through 47 illustrate a catheter device and an associated method suitable for deploying a medical device across a valve according to another aspect of the disclosed subject matter.

In an alternative embodiment, establishing the open configuration of the valves can be via the creation of a positive pressure within a vessel, e.g., introducing a fluid in an antegrade direction from a location upstream of the valve. Referring to FIG. 45, an exemplary embodiment of a device for creating a positive pressure is shown. The device 320 comprises an elongated catheter body 322 having a distal portion 324 and a proximal portion 326. The proximal portion 326 may include one or more ports 328 that are useful for communicating with the distal catheter end 330. For example, one port 328a can be a device port, which allows a device such as a guidewire to be advanced through the port into a lumen that runs the length of the catheter body. The device can be advanced through the device port 328a and catheter lumen to exit the distal end 330 of the catheter device. In addition, there can be an inflation port 328b near the proximal portion 326 that allows for an inflation fluid to communicate with the distal catheter portion 324 through an inflation lumen disposed within the catheter body.

The distal portion 324 of the catheter can include an occlusion balloon 332. This balloon 332 is can be formed from a compliant material, such as an elastomeric material. The balloon 332 is placed in communication with the inflation lumen of the catheter body, such that introduction of an inflation fluid through the inflation port 328b can cause the balloon to expand. When positioned within a body vessel, expansion of the balloon 332 can cause the vessel to be occluded.

Alternatively, the occlusion balloon need not be used, and instead the inflation port 328b can be used to communicate a fluid into the vessel that pressurizes it in order to open the venous valves. In this case, the "inflation port" can also be referred to as a "pressurization port." However, in the case where the catheter 320 does include an occlusion balloon 332, the catheter may further comprise a pressurization port 328c positioned near the proximal end of the catheter. This pressurization port 328c can communicate with a pressurization lumen disposed within the catheter body 322. The pressurization port 328c can attach to a syringe or another fluid source (not shown) in order to introduce a fluid or a gas into the patient anatomy through the distal end of the pressurization lumen. It will be appreciated that doing so while the catheter is located within a vein will cause blood to flow in the direction of decreasing venous pressure, i.e. when the distal end is placed above the jugular valves it will force blood in the antegrade direction. Arrow 334 shows the direction of fluid flow introduced by the catheter device.

Figure 46:
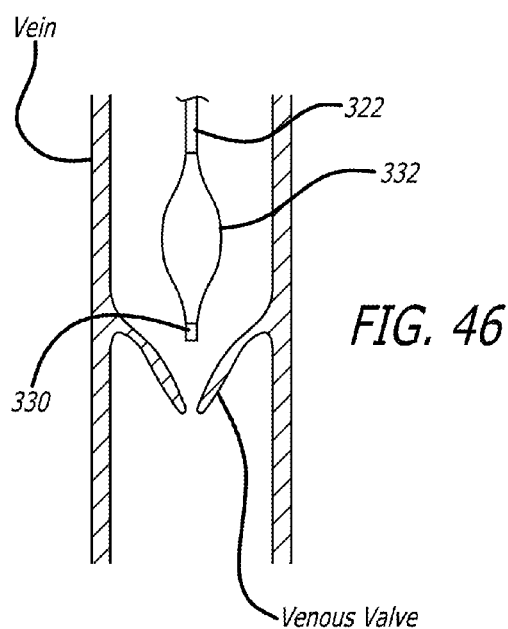

A method of using the device to introducing a fluid in an antegrade direction is illustrated in FIG. 46. The device such is a guidewire 336, can be advanced through the patient anatomy in an antegrade direction until the distal end is located near a venous valve. Access in an antegrade direction can be achieved in multiple ways. For example, the catheter can be introduced into the superior portion of the jugular vein using an introducer sheath placed in the neck of the patient. Alternatively, access can be achieved by first delivering the catheter through the external jugular vein or other collateral veins in order to introduce it in an antegrade direction in the internal jugular vein where those vessels meet. This approach can be used to access other veins in the antegrade direction as well.

After delivering the catheter in the antegrade direction within the target vessel, the occlusion balloon 322 disposed near the distal end of the device can be expanded by introducing an inflation fluid through the inflation port 328b. As the balloon 332 expands, it will contact the vessel wall and form a seal in the vessel, which prevents the antegrade flow of blood. It will be appreciated that this step can be omitted in the case of a device lacking an occlusion balloon, or in cases where the physician does not find it necessary to occlude the vessel, but would prefer to simply pressurize the vessel without the aid of occlusion.

Figure 47:
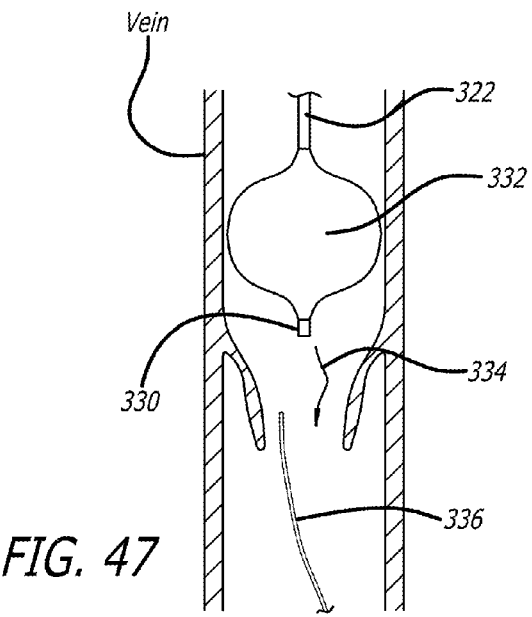

As shown in FIG. 47, when the vessel is occluded, positive pressure can be generated in the target vessel by introducing a fluid at a location proximate and upstream of the valve by a syringe or another fluid source. The pressure will result in the increased flow of blood in the antegrade direction as the injected fluid increases the volume of fluid and flow within the target vessel. While this flow is produced, the valves of the vein will tend to open due to the continuous antegrade blood flow. During this time when the valves are opened, the guidewire or another device 336 can be advanced through the device lumen into the vein in a retrograde direction. The device can advance freely through the valve without causing permanent damage to the valve because the valve will be dilated such that the passage of the device would not snag on the valve, or if it does, is more likely to deflect away and move through the vessel.

The method of producing increased antegrade flow and advancing a device to cross through a valve without damaging it can be performed repeated in an intermittent fashion. Fluid injection can be made at each point when the device is adjacent to, and ready to cross through, a valve. Alternatively, fluid injection can be made continuously the entire time that the device is being advanced through the vessel.

After a guidewire 336 is placed through the length of vessel that is intended to be treated, a medical device such as a stent or balloon catheter can be advanced over the guidewire and through the vessel length including the venous valves to the treatment site. This delivery can be aided through the use of positive flow as described above, as well.

In an alternative embodiment, establishing an open configuration of valves can be achieved by occluding a body lumen (e.g., a non-target vessel) proximal to and fluidly coupled with the target vessel in order to increase flow of blood through the target vessel. This increased blood flow or pressure will dilate the target vessel, which will be more conducive to passage of the guidewire in a retrograde direction without damaging the valve leaflets.

Figure 48:
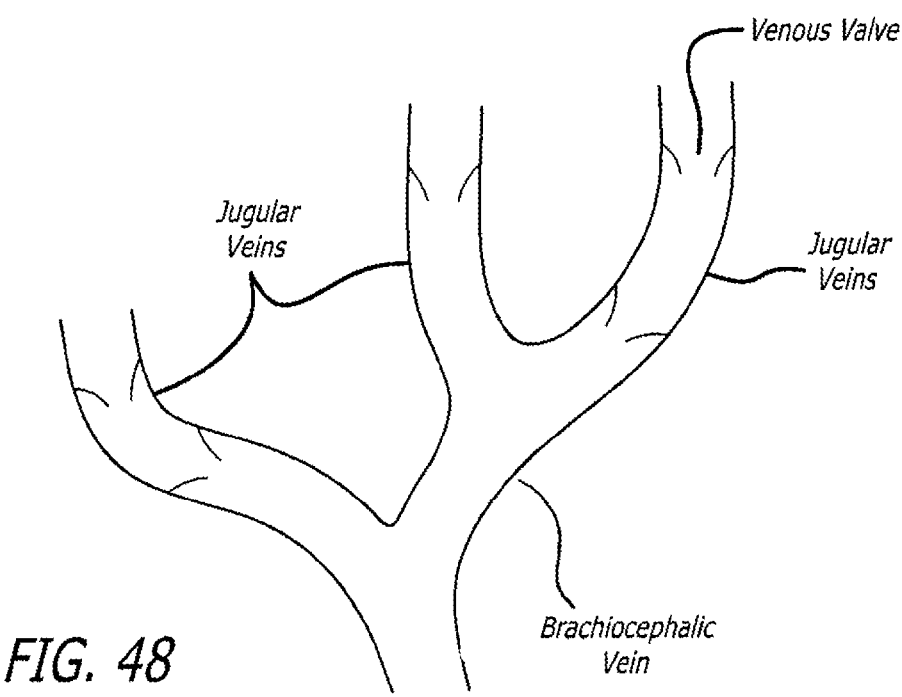
FIGS. 48 through 49 illustrate non-target vessel occlusion to dilate target vessel valves according to one embodiment of the disclosed subject matter.

FIG. 48 illustrates an example of the venous system in the neck region in which the jugular veins empty into the brachiocephalic vein. During the normal function of these veins, blood flow is in an antegrade direction as blood is pulsed through the body. During this time, the venous valves will open to permit the forward motion of blood. Retrograde flow of blood through the venous valves is prevented by the valve leaflets. These leaflets are capable of withstanding some back pressure, in order to ensure that blood is moved forward rather than simply pulsed back and forth. Therefore, the venous valves do not remain open at all times, but instead will open and close in synchronization with the flow of blood.

Figure 49:
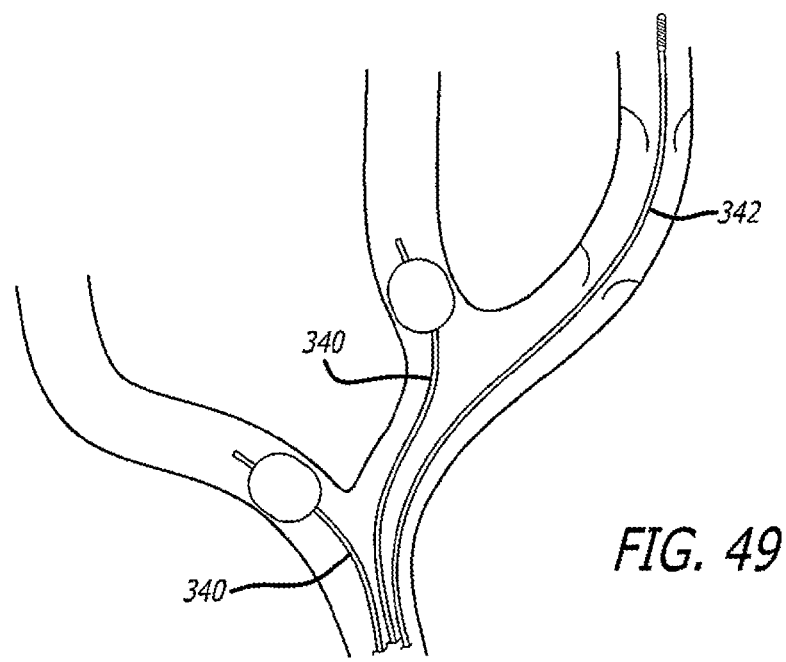

In order to prevent damage to the venous valves during retrograde delivery of a medical device, it is desirable for the valves to be opened. As illustrated in FIG. 49, one or more non-target vessels can be occluded, preferably in the region where the blood empties into the brachiocephalic vein on its way to the heart. The occlusion will redirect the flow of blood into other veins in order to ensure that the circulatory capacity of the vascular system remains constant. By redirecting this blood, at least some portion of the redirected blood will enter the target vessel. Thus, the flow through the target vessel will increase as a result of the reduction in flow through the non-target occluded vessel. As the venous valves are dilated after occlusion of a non-target vessel, a medical device can be delivered in a retrograde direction through the valves with less risk of damage to the valves. This is due to increased cross-sectional area of the vessel, which allows the crossing of a device. Therefore, the treatment region of the target vessel can be reached with greater ease and with less risk of residual vessel damage.

It is appreciated that more than one non-target vessel can be occluded in order to urge the dilation of the target vessel. The more blood is redirected toward the target vessel, the greater the chance that the venous valves will open entirely and permit passage of a medical device in the retrograde direction without damage. It will also be appreciated that although it is preferable that the venous valves will open entirely in the target vessel, partial dilation of the vein is also anticipated to ease device passage by reducing the likelihood that the device will snag and tear a venous valve.

Various techniques of occluding the non-target vessels can be used. For example, a balloon catheter can be used to achieve occlusion. A variety of balloon catheters exist which have compliant, non-compliant, or semi-compliant balloons. All of these varieties can be suitable for achieving occlusion. Furthermore, filter devices or expanding frames with occlusive sheaths can be used as well. When these frames are expanded within the patient anatomy, they will occlude their respective vessels and redirect blood flow. The redirected blood flow will cause the valves in connected vein to open, allowing a medical device such as a guidewire 342 and catheter (not shown) to be placed in the connected vein to allow a vascular procedure to be performed therein. Still other occlusive devices exist or can be developed by one skilled in the art in order to perform the occlusion.

Figure 57:
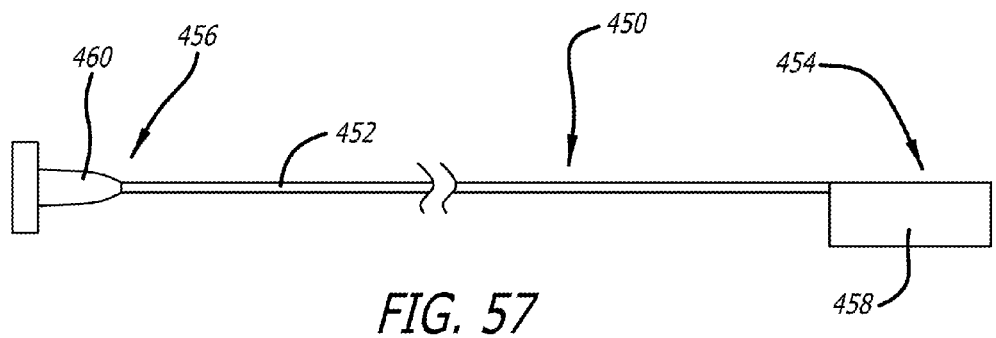
FIGS. 57 through 59 illustrate a catheter device having an expandable cuff and the associated method for opening a valve according to one aspect of the disclosed subject matter.

In an alternative embodiment, establishing the open configuration of a valve includes temporarily expanding an expandable cuff within the valve without permanently impacting the function of the valve. For example, a device can be provided with an expandable distal member having an outer surface and a central opening. The distal member can be used to expand a venous valve to allow a treatment device to be passed through the valve without causing damage to it. The valve can be expanded by the distal member when it is deployed within the valve, thereby causing the outer surface of the distal member to press upon the valve leaflets. While the distal member is expanded against the leaflets, the treatment device can be passed through the central opening of the distal member in order to access anatomies beyond the valve without damaging the valve during its travel. Such an embodiment is illustrated in FIG. 57. The device 450 includes an elongated catheter shaft 452 having a proximal end 454 and distal end 456. The catheter shaft 456 may further include one or more lumens capable of communicating fluids or bodies between the proximal and distal ends of the shaft.

An expandable distal member 458 can be positioned near the distal end of the catheter shaft. The distal member 458 can be a cuff, for example, that can be expanded or contracted between a delivery and deployment state. Expansion of the cuff 458 can occur, for example, through the introduction of a fluid into the cuff body, which produces inflation of the cuff 458 and expands it into the deployment state. Introduction of the fluid that enables this expansion may be affected by the delivery of an inflation fluid such as contrast media or saline into the cuff through an inflation lumen disposed within the catheter shaft. The inflation lumen can accordingly be connected to an inflation port 460 disposed near the proximal end of the catheter shaft. It is contemplated that this inflation port 460 may have a connection or fitting, such as a luer fitting by example which permits it to be removably coupled to a fluid source such as a syringe device.

Figure 58:
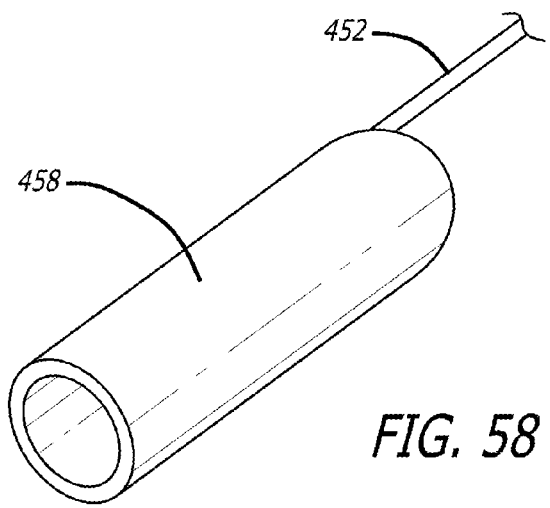

Referring to FIG. 58, a perspective view of an embodiment of a cuff member 458 is shown. The cuff member 458 can be generally tubular in shape when it is expanded into the deployed configuration. The tubular shape thus includes an outer surface that can be deployed against the valve leaflets and surround venous wall, and an internal cylindrical opening that allows a device to be passed through the cuff while it is expanded.

Various materials can be used to create the cuff member. For example, it is contemplated that typical balloon materials used in the manufacture of medical devices are particularly well suited to this application. This includes balloon materials of the compliant, semi-compliant, and even the compliant variety, which are well known in the art.

Figure 59:
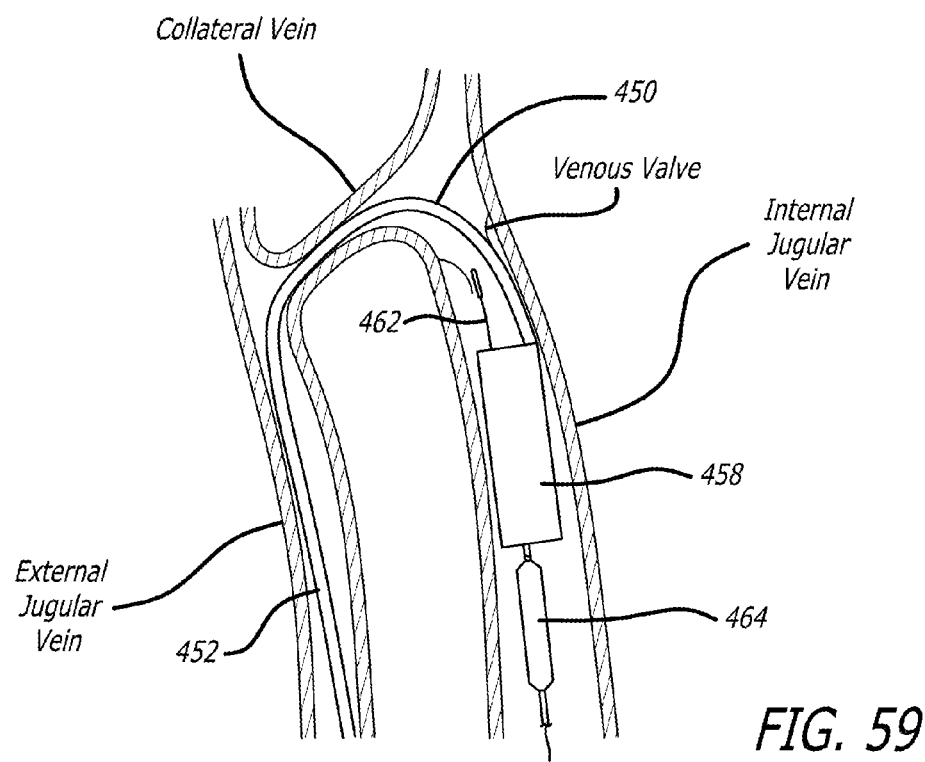

A method of delivering and deploying the device 450 within a patient anatomy is shown in FIG. 59. Here, the device 450 is first delivered in a retrograde fashion through the external jugular vein and other collateral veins until it reaches the internal jugular vein. It will be appreciated that alternative routes can be used to allow the device to enter the target vessel in a retrograde direction. For example, the device 450 can be introduced directly into the target vessel, or it can be introduced in an antegrade direction into a collateral vessel, through a venous puncture and access sheath positioned in the neck of the patient.

Once the device is positioned within the target vessel and the cuff member 498 is advanced into the valve or valves that must be crossed, the cuff member can be deployed. Again, this can be effected through the introduction of an inflation fluid in one embodiment. In an alternative embodiment, the cuff 458 can include an expandable framework, for example a frame comprised of a nitinol mesh, which could be expanded in a manner similar to that used for filter medical devices or self-expandable stent devices. In any case, once the cuff is expanded, it will press upon the valve leaflets and cause them to open toward the vein wall.

After the vein leaflets are opened, a treatment guidewire 462 and device 464 can be delivered in a retrograde direction through the cuff opening into the target anatomy. Alternatively, the treatment guidewire 462 and device 462 can be positioned adjacent to the inflated cuff member 458. After performing the desired procedure, which may for example by an angioplasty or stenting procedure of the target anatomy, the treatment devices 462 and 464 can be removed through the cuff and from the patient anatomy. It may also be possible to retrieve the cuff 458 from the patient anatomy while the treatment devices are still in place, since their retrieval will require that they be moved in the antegrade direction and is much less traumatic to the venous valves. Following retrieval of the treatment devices, the cuff member 458 can be contracted into a low profile configuration and it can be retrieved from the patient anatomy through its access route.

In accordance with another aspect of the subject matter, a method of deploying a medical device across a plurality of valves while minimizing trauma to these valves is provided. The method of deploying a medical device across a plurality of valves of a vessel of a patient, comprising: providing a catheter having an inner shaft member and an outer shaft member co-axially disposed and axially moveable relative to each other; positioning the catheter in a vessel having a plurality of valves including a first valve and a second valve; advancing a distal end of the outer shaft member across the first valve without permanently impacting the function of the first valve; moving the inner shaft member axially relative to the outer shaft member; and advancing a distal end of the inner shaft member across the second valve without permanently impacting the function of the second valve.

Figure 52:
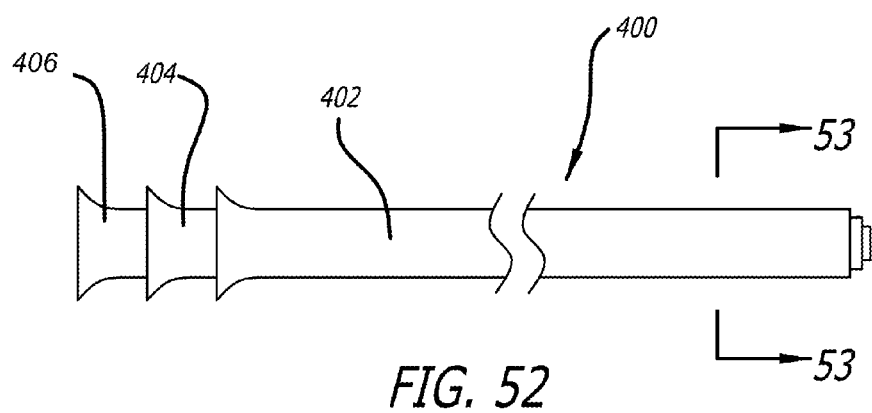
FIGS. 52 through 56 illustrate a telescoping catheter and a method of use thereof for deploying a medical device according to one aspect of the disclosed subject matter.

Referring to FIG. 52, a plan view of an exemplary telescoping catheter 400 is shown. The catheter has at least two catheter shafts placed concentrically relative to one another. The number of individual catheter shafts can be varied depending on the length of vessel that one would like to access. For example, if the operator intends to access a target site that requires passage through four venous valves, it may be beneficial to have a catheter with at least four independent catheter shafts. In the embodiment of FIG. 52, three catheter shafts 402, 404 and 406 are shown. The figure does not illustrate the proximal connections that the catheter can be fitted with to improve ease of use and function, but it will be appreciated by one skilled in the art that various connectors can be used.

A telescoping catheter 400 such as the one shown in FIG. 52 may include a proximal connection (not shown) that allows the catheter to be connected to a fluid source, such as a syringe. In this case, the connection may include a luer fitting (not shown) that can be coupled with a syringe so that fluid can be dispensed through the catheter.

Figure 53:
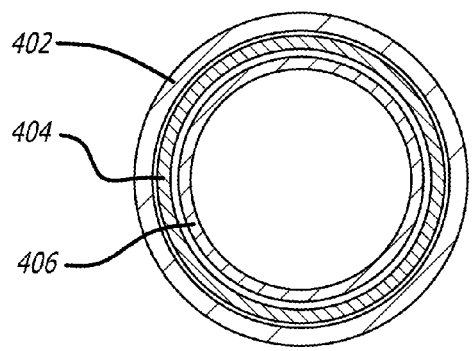

A cross-sectional view taken about line A-A of FIG. 52 is shown in FIG. 53. This illustrates the nested configuration of the telescoping catheter shafts 402, 404 and 406. As shown, there are at least three shaft members that are positioned concentrically. These shaft members can be advanced and retracted relative to one another by manually advancing or retracting the catheter shafts near their proximal ends. By doing so, the overall catheter length can be adjusted.

Figure 54:
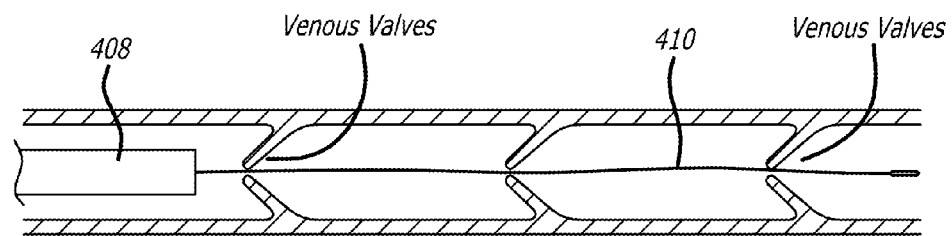

Referring to FIG. 54. the catheter can first be advanced through the patient anatomy until its distal end 408 is positioned near a valve leaflet. This can be done over a guidewire 410 that is placed in the anatomy first. The guidewire may thus be inserted through the entire target vessel length, or it may first be advanced only to the first valve to be advanced through in the manner described below.

Once the distal end 408 is positioned near the valve leaflet, the outer shaft member 402 can be slowly advanced through the valve leaflet. The distal end of the catheter (e.g., the distal end of each of the shaft members 402, 404, and 406) can be formed with an atraumatic configuration (not shown) that allows it to be advanced through the leaflet without caused leaflet damage. This atraumatic configuration can be formed through the use of a taper or a radius to allow them to be placed through the valve leaflets without puncturing or tearing them. Once the distal end of an outer shaft member is advanced through a valve leaflet, it is preferable that it not be advanced further, since the friction between the leaflet and the catheter outer surface could cause the leaflet to drag (e.g., in a retrograde direction), invert, tear, or otherwise be damaged.

Figure 55:
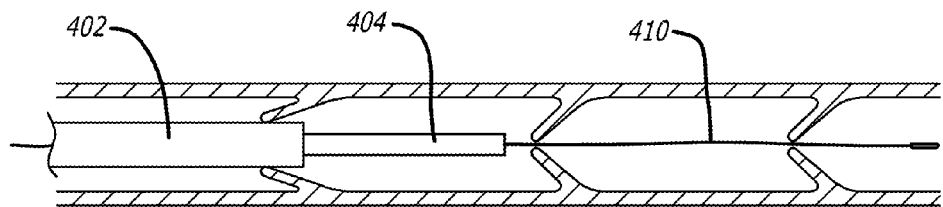

When the first valve is successfully crossed, the internal nested shaft members can be advanced. The motion of these internal catheters will not result in valve tearing because they are separated from the valves by the outer catheter. Therefore, they can be advanced up to the next valve that must be crossed, as shown in FIG. 55. Again, this advancement can be achieved with or without the use of an internal guidewire 410. When the next valve is reached, the distal end of an inner shaft member 404 can be advanced through the valve slowly to avoid damaging the valve. Again, once the valve is crossed, the shaft members that are internal to the previously advancing shaft can then be moved forward to repeat the crossing procedure at the next valve. This method of advancing through the valves can be continued until the target vessel region is reached.

Figure 56:
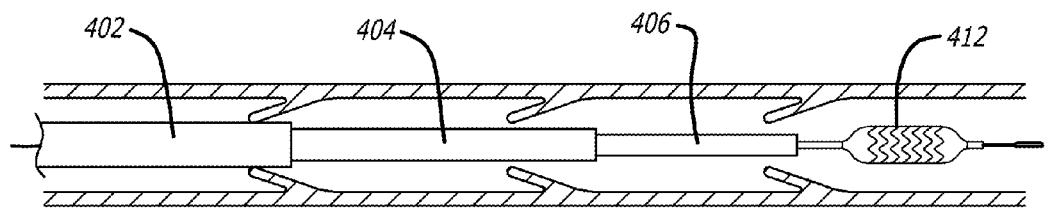

As shown in FIG. 56, after the target site is reached through the venous valves, a treatment device such as a balloon catheter or stent delivery system 412 can be inserted through the telescoping catheter to be positioned at the target site. The treatment device can then be deployed to treat the patient in the target area.

Recovery of the telescoping catheters can be made by retracting each of the catheter shaft members, e.g., in the reverse order as described above, until the entire telescoping catheter is removed from the patient anatomy.

Further to the various devices and methods of the disclosed subject matter as set forth above, a number of alternative methods of treatment, as described below, can be used as therapies for CCSVI for removing or displacing the obstructions within the venous system that cause blood reflux:

Thrombus Disintegration: This device category is generally directed at the use of thombolysis in order to restore normal blood flow in a vessel. For example, a catheter may be positioned near the site of occlusion in an internal jugular vein or another venous location that is responsible for producing blood reflux and CCSVI. The catheter can dispense medicaments to the venous location in order to dissolve blood clots or thrombus in those locations in order to restore blood flow. Numerous device embodiments can be used for this treatment. As an example, a double balloon occlusion catheter can be used in order to isolate the obstructed area for delivery of a lytic agent. Following delivery of the agent and the subsequent thrombus dissolution, the dissolved material may then either be allowed to pass into the distal vasculature by deflating the occlusion balloons or it may be removed through suction. It will be appreciated that thrombus disintegration can also be caused mechanically. For example, a device having a rotating wire may be used to act as a whisk within the vessel in order to disintegrate thrombus that is formed along the venous wall or disposed within the vein. Similar devices are used in the treatment of deep vein thrombosis. It may be beneficial to use a wire fabricated from a flexible material, such as nitinol. Furthermore, the device may easily use multiple wires to accomplish the desired task.

Thrombus Suction: Thrombus suction can be performed either before or after the occluded venous segment is treated with a lytic agent to dissolve the resident thrombus. In one example, a thrombolysis catheter may include an additional lumen with a port positioned near the area in which lytics are dispensed. By drawing a vacuum through that lumen, any dissolved thrombus can be removed from the vasculature. Alternatively, a suction catheter may be deployed prior to dissolution of any thrombus. By positioning the distal end of the catheter near the occluded vessel portion and drawing a vacuum, the clots or thrombus can be suctioned into the catheter and removed from the anatomy.

Covered Stent or Stent Graft: Another category of devices that would be helpful for treating the anatomies that are prevalent in CCSVI patients are covered stents or stent grafts. These devices are stent structures with a covering that is either a biological or synthetic substance. The covering is generally a thin film that can be adhered or otherwise connected to at least one location on the stent structure. Furthermore, the covering may be porous or non-porous and it may be loaded with a pro-healing or therapeutic agent, or not. By deploying a device of this type within an obstructed vein of a CCSVI patient, the obstruction can be opened to prevent blood reflow. This type of device can be particularly useful in the case of venous treatment because it will ensure that a vein valve will be opened up sufficiently in the case where the device is deployed across a valve. Therefore, the valve will not be allowed to recoil back into the vessel in order to obstruct blood flow and create reflux.

Atherectomy: Atherectomy can be a useful treatment for CCSVI because it allows obstructive tissue to be cut and removed from the patient, thereby creating a fully opened vessel and mitigating any risk of blood reflux. Numerous device types exist to allow this treatment, for example a directional-type atherectomy catheter can be used or a rotoblator-type device may be used, as well. In either case, the purpose of the atherectomy device is to resect the obstructive tissue that is causing venous obstruction. This tissue may be, for example, a lesion or a valve leaflet. In any case, after the tissue is resected it can either be removed from the patient or allowed to simply pass downstream in the blood flow. After removal of the tissue, the vein is anticipated to no longer have reflux caused by the removed tissue. Therefore, this may produce a beneficial impact on blood reflux and consequently multiple sclerosis.

Filter Device: It is contemplated that a filter device may be used in conjunction with one or more of the devices to ensure that the removed obstructive tissue is retrieved and removed from the patient. For example, a filter device can be used to capture tissue that has been ablated by a rotational-type atherectomy device, in order to ensure that the tissue is removed from the patient, as opposed to being allowed to pass downstream.

WallStent: A Wallstent design may be utilized for treatment of CCSVI. It is contemplated that the braided design may be optimally suited to the treatment of a vein due to its good flexibility and its comparatively low radial strength. By minimizing minimal strength, the likelihood of a vascular tear is decreased.

Thombolytics: Thrombolysis may be used to maintain a fluent venous system. This process will break down any clots, thrombus, or similar tissue that is obstructing the vein using therapeutic agents. For example, the infusion of tissue plasminogen activator (tPA) will stimulate fibrinolysis and the dissolution of plaques. After dissolving the obstructive tissue, the vein will allow blood flow without causing reflux.

Venous Bypass: It is contemplated that a venous bypass may be used to avoid blood reflux that causes the CCSVI condition. This is a surgical technique in which a vein is grafted across the portion of the vein that exhibits reflux. By doing so, sufficient blood flow is supported to prevent reflux from persisting and the CCSVI condition is thus treated.

Venous Transplant: In addition to venous bypass, another suitable procedure is a venous transplant in which the vein is replaced with a vein having minimal or no obstructions. Thus, the blood reflux is eliminated in order to treat the CCSVI.

Ultrasonic Disruption: An alternative therapy for opening veins contributing to CCSVI is the use of ultrasonic disruption. In this procedure, an ultrasonic energy source directs energy toward an obstructive tissue either intravascularly or extracorporeally. The obstruction is thus disrupted and disintegrated in order to open the vein passage and to allow good blood flow without reflux. It may be beneficial to use a filter in this case.

Micro-Bubble Disruption: Microbubble disruption utilizes the creation of microbubbles in the region of venous obstruction to cause the obstructive tissue to be disrupted and disintegrated, thus opening the venous passage and preventing reflux. In order to produce the microbubbles, techniques such as energization of gold microparticles or energization of micromaterials may be used to cause localized expansion of gases within the blood flow that create bubbles. The bubbles subsequently implode, producing energy that disrupts the adjacent venous obstruction.

Valve Implant: A valve implant may be positioned within the vein that exhibits reflux in order to prevent the reflux. One type of valve that is particularly useful for this is a one-way valve, such as a duck-bill type valve. The one-way valve would allow blood to flow in one direction, but would prevent reflux into the vein when downstream pressure increases.

Each of the therapies discussed above provide an alternative treatment to stents that avoids the risk of a stent dislodging and causing complications within the heart.

While illustrative embodiments of the invention have been disclosed herein, numerous modifications and other embodiments may be devised by those skilled in the art in accordance with the invention. For example, the various features depicted and described in the embodiments herein can be altered or combined to obtain desired scaffold characteristics in accordance with the invention. Therefore, it will be understood that the appended claims are intended to include such modifications and embodiments, which are within the spirit and scope of the present invention.

The invention claimed is:

1. A method of fabricating an intraluminal scaffold, comprising:
   providing a non-cylindrical tubular body having a substantially uniform wall thickness with a lumen defined therethrough, at least a length of the non-cylindrical tubular body having an enlarged portion;
   defining a plurality of cells in the non-cylindrical tubular body to form an intraluminal scaffold capable of having a substantially cylindrical shape in a compressed condition for delivery and an expanded condition for implant within a vessel, the at least a length of the non-cylindrical tubular body having the enlarged portion when in the expanded condition.

2. The method of claim 1, wherein providing the non-cylindrical tubular body includes extruding a generally cylindrical tube, and expanding at least a portion of the cylindrical tube to form the enlarged portion.

3. The method of claim 2, wherein expanding at least the portion of the cylindrical tube includes blow molding to form the enlarged portion.

4. The method of claim 2, wherein expanding at least the portion of the cylindrical tube includes hydroforming the enlarged portion.

5. The method of claim 2, wherein the non-cylindrical tubular body is made of a polymeric material.

6. The method of claim 1, wherein providing the non-cylindrical tubular body includes depositing tubular body material on a mandrel having a surface defining the enlarged portion.

7. The method of claim 6, wherein the non-cylindrical tubular body material includes a metal or metal alloy.

8. The method of claim 6, wherein defining the plurality of cells in the non-cylindrical tubular body includes depositing the tubular body material on select locations of the surface of the mandrel.

9. The method of claim 1, wherein defining the plurality of cells in the non-cylindrical tubular body includes removing material from the tubular body.

10. The method of claim 9, wherein removing material from the non-cylindrical tubular body includes laser cutting the non-cylindrical tubular body.

11. The method of claim 1, wherein the plurality of cells are uniform in size and shape.

12. The method of claim 1, wherein the plurality of cells are nonuniform in size or shape.

13. The method of claim 1, wherein the enlarged portion of the non-cylindrical tubular body has a non-cylindrical shape.

14. The method of claim 1, wherein the enlarged portion of the non-cylindrical tubular body has a generally bulbous shape in the expanded condition.

15. The method claim 1, wherein the enlarged portion of the non-cylindrical tubular body defines a spiral anchor.

16. The method of claim 1, wherein the enlarged portion of the non-cylindrical tubular body has a generally buttercup shape in the expanded condition.

17. The method of claim 1, wherein the enlarged portion is spaced from an end of the non-cylindrical tubular body.

18. The method of claim 1, wherein the non-cylindrical tubular body has a plurality of enlarged portions.

19. The method of claim 18, wherein the non-cylindrical tubular body has a dumbbell shape defined by the plurality of enlarged portions when in the expanded condition.

20. The method of claim 18, wherein the non-cylindrical tubular body has a pine cone shape defined by the plurality of enlarged portions when in the expanded condition.

* * * * *